US011771904B2

(12) United States Patent
Boor et al.

(10) Patent No.: US 11,771,904 B2
(45) Date of Patent: Oct. 3, 2023

(54) DIAGNOSTIC CIRCUITRY FOR MONITORING CHARGE STATES OF ELECTRODES OF A LEAD SYSTEM ASSOCIATED WITH AN IMPLANTABLE PULSE GENERATOR

(71) Applicant: ADVANCED NEUROMODULATION SYSTEMS, INC., Plano, TX (US)

(72) Inventors: Steven Boor, Plano, TX (US); Daran DeShazo, Lewisville, TX (US)

(73) Assignee: Advanced Neuromodulation Systems, Inc., Plano, TX (US)

( * ) Notice: Subject to any disclaimer, the term of this patent is extended or adjusted under 35 U.S.C. 154(b) by 452 days.

(21) Appl. No.: 16/917,199

(22) Filed: Jun. 30, 2020

(65) Prior Publication Data

US 2021/0275819 A1 Sep. 9, 2021

Related U.S. Application Data

(60) Provisional application No. 62/984,524, filed on Mar. 3, 2020.

(51) Int. Cl.
*A61N 1/36* (2006.01)
*A61N 1/39* (2006.01)
(Continued)

(52) U.S. Cl.
CPC .......... *A61N 1/36178* (2013.01); *A61B 5/304* (2021.01); *A61N 1/36038* (2017.08);
(Continued)

(58) Field of Classification Search
None
See application file for complete search history.

(56) References Cited

U.S. PATENT DOCUMENTS

| 4,499,552 A | 2/1985 | Kanazawa |
| 5,540,235 A * | 7/1996 | Wilson ................ A61B 5/4047 |
| | | 600/545 |

(Continued)

FOREIGN PATENT DOCUMENTS

| WO | 2001093953 A1 | 12/2001 |
| WO | 2006014972 A2 | 2/2006 |

OTHER PUBLICATIONS

Jim Keith. "Kelvin Connection". https://www.electroschematics.com/kelvin-connection/, posted at least as of Sep. 19, 2014 per the comment, viewed on Nov. 3, 2022 (Year: 2014).*

(Continued)

*Primary Examiner* — Erica S Lee
(74) *Attorney, Agent, or Firm* — Norton Rose Fulbright US LLP

(57) ABSTRACT

A system and method for measuring and monitoring charge states of one or more electrodes of an implanted stimulation lead system associated with an IPG. A Kelvin connection scheme operative with a switching circuit is provided for coupling select electrode terminals disposed in a Kelvin connection measurement loop in a switchable manner to sense and reference inputs of an analog-to-digital converter (ADC) configured as at least part of diagnostic circuitry for the IPG.

20 Claims, 9 Drawing Sheets

(51) Int. Cl.
*A61B 5/304* (2021.01)
*A61N 1/37* (2006.01)

(52) U.S. Cl.
CPC ..... *A61N 1/36053* (2013.01); *A61N 1/36062* (2017.08); *A61N 1/36114* (2013.01); *A61N 1/36128* (2013.01); *A61N 1/36175* (2013.01); *A61N 1/37* (2013.01); *A61N 1/3704* (2013.01); *A61N 1/39622* (2017.08)

(56) References Cited

U.S. PATENT DOCUMENTS

| | | |
|---|---|---|
| 5,700,280 A | 12/1997 | Silvian |
| 6,609,031 B1 | 8/2003 | Law et al. |
| 7,180,780 B1 | 2/2007 | Varrichio et al. |
| 7,212,110 B1 | 5/2007 | Martin et al. |
| 7,228,179 B2 | 6/2007 | Campen et al. |
| 7,571,007 B2 | 8/2009 | Erickson et al. |
| 7,937,158 B2 | 5/2011 | Erickson et al. |
| 8,498,698 B2 | 7/2013 | Donofrio |
| 9,054,436 B2 | 6/2015 | Swanson et al. |
| 9,533,164 B2 | 1/2017 | Erickson et al. |
| 9,984,691 B2 | 2/2018 | Hellman et al. |
| 11,160,984 B2 | 11/2021 | DeShazo et al. |
| 11,331,477 B2 | 5/2022 | Boor et al. |
| 2003/0199944 A1 | 10/2003 | Chapin et al. |
| 2005/0010121 A1 | 1/2005 | Ross et al. |
| 2005/0107841 A1 | 5/2005 | Meadows et al. |
| 2006/0170486 A1 | 8/2006 | Tranchina et al. |
| 2006/0173493 A1 | 8/2006 | Armstrong et al. |
| 2008/0015641 A1* | 1/2008 | Armstrong ......... A61N 1/36153 607/2 |
| 2009/0048643 A1 | 2/2009 | Erickson et al. |
| 2011/0160803 A1 | 6/2011 | Stessman et al. |
| 2011/0160822 A1 | 6/2011 | Jackson et al. |
| 2013/0053678 A1 | 2/2013 | Vitek et al. |
| 2013/0190634 A1 | 7/2013 | Phillips |
| 2013/0325085 A1 | 12/2013 | Carbunaru et al. |
| 2014/0084949 A1 | 3/2014 | Smith et al. |
| 2014/0343628 A1 | 11/2014 | Kaula et al. |
| 2017/0001010 A1 | 1/2017 | Bradley et al. |
| 2017/0209703 A1 | 7/2017 | Jiang et al. |
| 2017/0259065 A1 | 9/2017 | Baru et al. |
| 2019/0170832 A1 | 6/2019 | Kravljaca et al. |
| 2019/0255333 A1* | 8/2019 | Baru ................. A61N 1/36153 |
| 2020/0155851 A1 | 5/2020 | Boor et al. |
| 2020/0306543 A1 | 10/2020 | Boor et al. |

OTHER PUBLICATIONS

Patent Cooperation Treaty, International Search Report and Written Opinion issued for PCT Application No. PCT/US2020/066846, dated Mar. 23, 2021, 8 pages.

International Search Report, dated May 22, 2020, Application No. PCT/US2020/021802, pp. 4.

International Search Report, dated May 27, 2020, Application No. PCT/US2020/021806, pp. 2.

Circuitry for Using High-Speed Low-Power Voltage Comparator for Compliance Voltage Monitoring in Current-Mode Neurostimulator, IP.com, Apr. 4, 2002, 5 pgs., IPCom.

High-Speed Low-Power Voltage Comparator to Facilitate Automatic Compliance Voltage Control for a Neurostimulator, IP.com, Jul. 18, 2003, 12 pgs., IPCom.

* cited by examiner

SETTING A KELVIN CONNECTION SELECTION MODE TO CONFIGURE A PLURALITY OF SWITCHES TO EFFECTUATE DIFFERENT COMBINATIONS OF VOLTAGE MEASUREMENT CONNECTION PATHS BETWEEN THE TERMINALS OF THE ELECTRODES AND THE SENSE AND REFERENCE INPUTS OF THE ADC OF THE DIAGNOSTIC CIRCUITRY — 420

CONFIGURING THE AT LEAST ONE INACTIVE ELECTRODE AS A DEDICATED KELVIN ELECTRODE OF THE IMPLANTABLE LEAD SYSTEM FOR FACILITATING AT LEAST ONE KELVIN CONNECTION PATH FOR MEASURING VOLTAGES RESPECTIVELY ASSOCIATED WITH ONE OR MORE ACTIVE ELECTRODES OF THE IMPLANTABLE LEAD SYSTEM — 430

CONFIGURING THE AT LEAST ONE ACTIVE ELECTRODE AS ONE OF A CATHODE TO PROVIDE CATHODIC STIMULATION TO THE BIOLOGICAL TISSUE AND AN ANODE TO PROVIDE ANODIC STIMULATION TO THE BIOLOGICAL TISSUE — 440

DIAGNOSTIC CIRCUITRY FOR MONITORING CHARGE STATES OF ELECTRODES OF A LEAD SYSTEM ASSOCIATED WITH AN IMPLANTABLE PULSE GENERATOR

PRIORITY AND CROSS-REFERENCE TO RELATED APPLICATION(S)

This nonprovisional application claims priority based upon the following prior United States provisional patent application(s): (i) "DIAGNOSTIC CIRCUITRY FOR MONITORING CHARGE STATES OF ELECTRODES OF A LEAD SYSTEM ASSOCIATED WITH AN IMPLANTABLE PULSE GENERATOR", Application No. 62/984,524, filed Mar. 3, 2020, in the name(s) of Steven Boor and Daran DeShazo; each of which is hereby incorporated by reference in its entirety.

TECHNICAL FIELD

The present disclosure generally relates to implantable pulse generators and circuitry associated therewith. More particularly, and not by way of any limitation, the present disclosure is directed to diagnostic circuitry for an implantable pulse generator (IPG) used in stimulation therapy, the diagnostic circuitry operative with respect to monitoring charge states of electrode capacitances of an implantable lead system associated with the IPG.

BACKGROUND

The use of electronic stimulation systems to control pain or other indications, or to otherwise provide therapy, by nerve or muscle stimulation has been in use for a number of years. For example, spinal cord stimulation (SCS) is a technique that has been used for pain management since the 1960s. Stimulation systems may also be used in stimulating areas other than the spinal cord, such as for deep brain stimulation, muscle stimulation, etc.

Stimulation systems often comprise a pulse generator coupled to one or more implanted therapy delivery leads having a plurality of electrodes disposed in an area in which neurostimulation is desired. Alternatively, stimulation systems may comprise a micro-stimulation system in which a small implantable housing having electrodes thereon includes a pulse generator, wherein the entire micro-stimulation system is disposed in an area in which neurostimulation is desired. Of course, all or a portion of a stimulation system need not be implanted into a body to provide a desired therapy.

A stimulation system pulse generator may be provided in various configurations, such as a totally implanted pulse generator (IPG) or a radio frequency (RF)-based system. A typical IPG configuration comprises a surgically implanted, internally-powered pulse generator and a multi-electrode lead. A typical RF system configuration comprises a surgically implanted passive receiver and leads, and a transmitter which is worn externally. In operation, the transmitter communicates, through an RF signal, to the implanted receiver to provide stimulation energy and control.

In an SCS application, lead electrodes which are used with an example pulse generator, such as any of the foregoing pulse generators, to deliver a particularized electric field via stimulation to a specific region of the spinal cord or surrounding tissue are considered as the "active" electrodes of the IPG for therapy delivery; unused or "inactive" electrodes are the ones not used for stimulation therapy. Applying such an electric field with the active electrodes across one or more nerve bundles and/or nerve roots, if properly directed and produced at the necessary levels, can "mask" certain forms of chronic pain in a phenomenon referred to as "paresthesia". Similarly, applying an electric field across other tissue, such as muscle or brain matter, near which such electrodes are disposed may provide a desired therapy. The focus, characteristics and intensity of the generated electric field are determined by the electrode configuration (the polarity, if any, assumed by each electrode) and the properties of an electric pulse waveform, which may generally include a stimulation frequency, a stimulation pulse width, a stimulation amplitude, discharge method, and phase information, etc. (collectively "stimulation settings" or "stim-sets").

Chronically implantable electrical stimulation mechanisms have been the focus of advanced physiological engineering research for the past few decades. With the advent of microelectronics, it has become imperative to investigate the criticality of safe functional electrical stimulation for large electrode arrays since stimulation electrode characteristics can change due to electrode dissolution/deterioration during prolonged use. Structural damage can occur if there is exposure to electrode potential much higher than applicable electrochemical windows associated with a tissue interface. Moreover, with large stimulation arrays employed in certain applications, monitoring the charge status of different electrodes becomes challenging.

Whereas advances in IPG systems and associated stimulation circuitry for use in various therapy applications continue to grow apace, several lacunae remain, thereby requiring further innovation as will be set forth hereinbelow.

SUMMARY

Embodiments of the present patent disclosure are broadly directed to implantable pulse generators or other medical devices (IPG/IMD), systems and associated diagnostic circuitry wherein various types of Kelvin connection schemes may be provided for effectuating voltage and charge state measurements with respect to one or more electrodes of a stimulation lead system associated with an IMG/IMD system. In one arrangement, a system and method is disclosed for measuring and monitoring charge states of capacitive components associated with one or more electrodes of the implanted stimulation lead system. A Kelvin connection scheme operative with a switching circuit is provided for coupling select electrode terminals disposed in a Kelvin connection measurement loop in a switchable manner to sense and reference inputs of an analog-to-digital converter (ADC) configured as at least part of diagnostic circuitry for the IPG.

In one aspect, an implantable medical device (IMD) having advanced/enhanced diagnostic capabilities is disclosed. According to an example embodiment, the IMD comprises, inter alia, a power supply module; a processing unit; a pulse generator; and an implantable lead system including at least one lead having a plurality of electrodes adapted to stimulate a patient's tissue responsive to instructions generated by the processing unit in association with the pulse generator, the plurality of electrodes including at least one inactive electrode and at least one active electrode. The IMD also includes diagnostic circuitry comprising an analog-to-digital converter (ADC) having a sense input and a reference input, and switching circuitry operative to selectively couple one or more terminals associated with each electrode to the sense and reference inputs of the ADC. In one variation, the switching circuitry may include one or more switches for each electrode corresponding to the one or more terminals associated with the electrode. The diagnostic circuitry may be configured to perform following acts in conjunction with the switching circuitry and the processing unit: utilize one of a direct current (DC) blocking stimulation capacitor ($C_{DC}$) terminal and an alternating current (AC) coupling sense capacitor ($C_{SENSE}$) terminal of the at least one inactive electrode of the implantable lead system as a first Kelvin connection terminal switchably coupled by the switching circuitry to the reference input of the ADC for a voltage measurement with respect to a second active electrode of the implantable lead system; utilize an AC coupling sense capacitor ($C_{SENSE}$) terminal or a DC blocking stimulation capacitor ($C_{DC}$) terminal of the second active electrode switchably coupled by the switching circuitry as a second Kelvin connection terminal to the sense input of the ADC for the voltage measurement; and obtain the voltage measurement across the first and second Kelvin connection terminals as a voltage indicative of a charge state accumulated across at least one of a $C_{DC}$ capacitor coupled to the second active electrode and a double-layer (DL) capacitance ($C_{DL}$) associated with an electrode/tissue interface (ETI) of the second active electrode. In one variation, the IMD may also comprise a mode selector operative to configure the switching circuitry to effectuate different combinations of voltage measurement connection paths or loops between the electrode terminals and the sense and reference inputs of the ADC of the diagnostic circuitry.

In another aspect, a method is disclosed for obtaining electrode charge state information associated with an IMD's implantable lead system. The method comprises, inter alia, configuring a plurality of electrodes of the IMD's lead system as having at least one active electrode and at least one inactive node and performing switchable coupling of a select active electrode terminal and an unused electrode terminal to diagnostic circuitry for facilitating voltage measurement. In one embodiment, the method may involve switchably coupling one of a direct current (DC) blocking stimulation capacitor ($C_{DC}$) terminal and an alternating current (AC) coupling sense capacitor ($C_{SENSE}$) terminal of the at least one inactive electrode of the implantable lead system as a first Kelvin connection terminal to a reference input of an ADC forming diagnostic circuitry for a voltage measurement with respect to a second active electrode of the implantable lead system; and switchably coupling an AC coupling sense capacitor ($C_{SENSE}$) terminal or a DC blocking stimulation capacitor ($C_{DC}$) terminal of the second active electrode as a second Kelvin connection terminal to a sense input of the ADC. The voltage measurement may therefore be obtained across the first and second Kelvin connection terminals as a voltage indicative of a charge state accumulated across at least one of a $C_{DC}$ capacitor coupled to the second active electrode and a double-layer (DL) capacitance ($C_{DL}$) associated with an electrode/tissue interface (ETI) of the second active electrode. In one variation, an example method may further comprise setting or otherwise selecting a Kelvin connection selection mode in order to configure a plurality of switches to effectuate different combinations of voltage measurement connection paths or loops between the electrode terminals and the sense and reference inputs of the ADC of the diagnostic circuitry. In another variation, an example method may comprise configuring at least one inactive electrode of the implantable lead system as a dedicated Kelvin electrode for facilitating at least one Kelvin connection path with respect to measuring voltages respectively associated with one or more active electrodes of the implantable lead system.

In another aspect, an embodiment of a biostimulation system is disclosed wherein diagnostic circuitry and switching circuitry operative with a Kelvin connection arrangement of an IMD may be configured to facilitate voltage/charge state measurements in response to program instructions executed by an external programmer device disposed in a communicative relationship with the IMD. In an example implementation, terminals of a DC blocking stimulation capacitor or an AC-coupling sense capacitor associated with an inactive electrode of the lead system may be configured as one Kelvin connection terminal or node of a measurement circuit path that may be switchably connected to an ADC's reference input whereas a counter Kelvin connection terminal or node with respect to a select active electrode is effectuated across the electrode/tissue interface using either a DC blocking stimulation capacitor or an AC-coupling sense capacitor provided therewith, which may be switchably connected to the ADC's sense input.

Example embodiments may therefore be configured to provide a scheme for measuring and monitoring the voltages and charge states of stimulation leads, individual electrodes, and individual DC blocking capacitors under suitable programmatic control, which advantageously allows for novel and/or enhanced system-level diagnostic capabilities in an IPG/IMD. Further, such new capabilities and functionalities can also be utilized for optimizing stimulation efficiency and/or efficacy, improving battery longevity, as well as for providing stimulation lead integrity monitoring, electrode reliability, and patient safety.

Additional/alternative features and variations of the embodiments will be apparent in view of the following description and accompanying Figures.

BRIEF DESCRIPTION OF THE DRAWINGS

Embodiments of the present disclosure are illustrated by way of example, and not by way of limitation, in the Figures of the accompanying drawings in which like references indicate similar elements. It should be noted that different references to "an" or "one" embodiment in this disclosure are not necessarily to the same embodiment, and such references may mean at least one. Further, when a particular feature, structure, or characteristic is described in connection with an embodiment, it is submitted that it is within the knowledge of one skilled in the art to effectuate such feature, structure, or characteristic in connection with other embodiments whether or not explicitly described.

The accompanying drawings are incorporated into and form a part of the specification to illustrate one or more exemplary embodiments of the present disclosure. Various advantages and features of the disclosure will be understood from the following Detailed Description taken in connection with the appended claims and with reference to the attached drawing Figures in which:

FIGS. 4A-4D depict flowcharts illustrative of blocks, steps and/or acts that may be (re)combined in one or more arrangements with or without other flowcharts for monitoring the charge states of an IPG/IMD lead system according to some embodiments of the present disclosure.

DETAILED DESCRIPTION

Figure 1A:
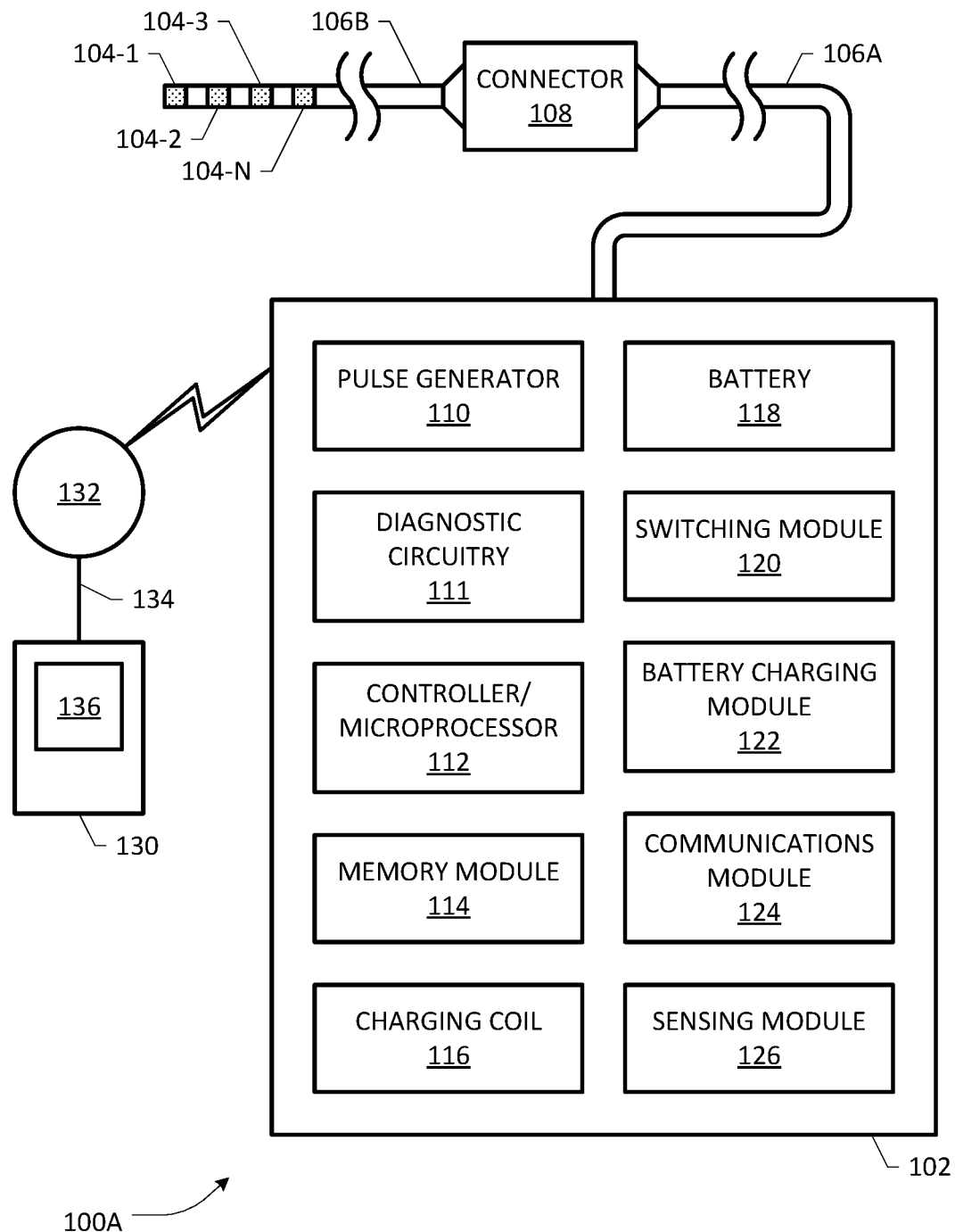
FIG. 1A depicts an example biostimulation system wherein one or more embodiments of a diagnostic circuit of the present disclosure may be practiced in accordance with the teachings herein.

In the description herein for embodiments of the present disclosure, numerous specific details are provided, such as examples of circuits, devices, components and/or methods, to provide a thorough understanding of embodiments of the present disclosure. One skilled in the relevant art will recognize, however, that an embodiment of the disclosure can be practiced without one or more of the specific details, or with other apparatuses, systems, assemblies, methods, components, materials, parts, and/or the like. In other instances, well-known structures, materials, or operations are not specifically shown or described in detail to avoid obscuring aspects of embodiments of the present disclosure. Accordingly, it will be appreciated by one skilled in the art that the embodiments of the present disclosure may be practiced without such specific components. It should be further recognized that those of ordinary skill in the art, with the aid of the Detailed Description set forth herein and taking reference to the accompanying drawings, will be able to make and use one or more embodiments without undue experimentation.

Additionally, terms such as "coupled" and "connected," along with their derivatives, may be used in the following description, claims, or both. It should be understood that these terms are not necessarily intended as synonyms for each other. "Coupled" may be used to indicate that two or more elements, which may or may not be in direct physical or electrical contact with each other, co-operate or interact with each other. "Connected" may be used to indicate the establishment of communication, i.e., a communicative relationship, between two or more elements that are coupled with each other. Further, in one or more example embodiments set forth herein, generally speaking, an electrical element, component or module may be configured to perform a function if the element may be programmed for performing or otherwise structurally arranged to perform that function.

Some embodiments described herein may be particularly set forth in the context of an implantable pulse generator (IPG) for generating electrical stimulation for application to a desired area of a body or tissue based on a suitable stimulation therapy application, such as a spinal cord stimulation (SCS) system. However, it should be understood that example circuitry and methods of operation disclosed herein are not limited thereto, but have broad applicability, including but not limited to different types of implantable devices such as neuromuscular stimulators and sensors, dorsal root ganglion (DRG) stimulators, deep brain stimulators, cochlear stimulators, retinal implanters, muscle stimulators, tissue stimulators, cardiac stimulators, gastric stimulators, and the like, including other bioelectrical sensors and sensing systems, which may be broadly referred to as "biostimulation" applications and/or implantable medical devices (IMDs) for purposes of the present disclosure. Moreover, example circuitry and methods of operation disclosed herein are not limited to use with respect to an IPG or any particular form of IPG. For example, some embodiments may be implemented with respect to a fully implantable pulse generator, a radio frequency (RF) pulse generator, an external pulse generator, a micro-implantable pulse generator, inter alia.

Referring to FIG. 1A in particular, depicted therein is a biostimulation system or IMD system 100A wherein one or more embodiments of a diagnostic scheme or circuit of the present patent disclosure may be practiced for monitoring charge states of various capacitive components of an electrode/tissue interface (ETI) equivalent circuit arrangement associated with implanted lead electrodes in accordance with the teachings herein. By way of illustration, system 100A may be adapted to stimulate spinal cord tissue, peripheral nerve tissue, deep brain tissue, DRG tissue, cortical tissue, cardiac tissue, digestive tissue, pelvic floor tissue, or any other suitable biological tissue of interest within a patient's body, as noted above. System 100A includes an implantable pulse generator (IPG) or IMD 102 that comprises a diagnostic circuit module 111 adapted to effectuate Kelvin connections with one or more electrodes of an implantable lead system for measuring voltages associated with the stimulated electrodes as will be set forth in additional detail further below. In one example embodiment, IPG 102 may be implemented as having a metallic housing or can that encloses a controller/processing block or module 112, pulse generating circuitry 110, a charging coil 116, a battery 118, a far-field and/or near field communication block or module 124, battery charging circuitry 122, switching circuitry 120, sensing circuitry 126, a memory module 114, and the like. Controller/processor module 112 typically includes a microcontroller or other suitable processor for controlling the various other components of IPG/IMD 102. Software/firmware code may be stored in memory 114 of IPG 102, which may be integrated with the controller/processor module 112, and/or other suitable application-specific storage components (not particularly shown in this FIG.) for execution by the microcontroller or processor 112 and/or other programmable logic blocks to control the various components of the device for purposes of an embodiment of the present patent disclosure.

In one arrangement, IPG 102 may be coupled to a separate or an attached extension component 106A for providing electrical and physical connectivity to an implantable lead system 106B via a lead connector 108, wherein a distal end of the lead 106B includes a plurality of electrodes 104-1 to 104-N. Where the extension component 106A is provided as a separate component, the extension component 106A may connect with a "header" portion of IPG 102 as is known in the art. If the extension component 106A is integrated with IPG 102, internal electrical connections may be made through respective conductive components. In general, electrical pulses are generated by the pulse generating circuitry 110 under the control of processing block 112, and are provided to the switching circuitry 120 that is operative to selectively connect to electrical outputs of the IPG device, which are ultimately coupled to the electrodes 104-1 to 104-N at a distal end of the lead system 106B via respective electrical conductive traces.

In one arrangement, lead electrodes 104-1 to 104-N may be positioned along an axis of the lead 106B, with an angular offset such that the lead electrodes 104-1 to 104-N do not overlap. The lead electrodes 104-1 to 104-N may be in the shape of a ring such that each lead electrode continuously covers the circumference of the exterior surface of the lead 106B. Typically, the lead electrodes 104-1 to 104-N are separated from each other by non-conducting portions of the lead 106B, which electrically isolate each lead electrode 104-1 to 104-N from an adjacent lead electrode 104-1 to 104-N. The non-conducting portions of the lead 106B may include one or more insulative materials and/or biocompatible materials to allow the lead 106B to be implantable within the patient. Non-limiting examples of such materials include polyimide, polyetheretherketone (PEEK), polyethylene terephthalate (PET) film (also known as polyester or Mylar), polytetrafluoroethylene (PTFE) (e.g., Teflon), or parylene coating, polyether bloc amides, polyurethane, or the like compositions.

Additionally or alternatively, electrodes 104-1 to 104-N may be in the shape of a split or non-continuous ring such that the stimulation pulse(s) may be emitted in a manner so as to create an electric field emanating in an outward radial direction adjacent to the lead electrodes 104-1 to 104-N. Examples of lead electrodes 104-1 to 104-N and associated fabrication processes are disclosed in one or more of the following: (i) U.S. Patent Application Publication No. 2011/0072657, entitled, "METHOD OF FABRICATING STIMULATION LEAD FOR APPLYING ELECTRICAL STIMULATION TO TISSUE OF A PATIENT"; and (ii) U.S. Patent Application Publication No. 2018/0008821, entitled, "IMPLANTABLE THIN FILM DEVICES", each of which is incorporated herein by reference.

It should be noted the lead electrodes 104-1 to 104-N may be in various other formations, for example, in a planar formation, in an array or grid, etc. on a paddle structure as disclosed in U.S. Patent Application Publication No. 2014/0343564, entitled, "PADDLE LEADS FOR NEUROSTIMULATION AND METHOD OF DELIVERYING THE SAME", which is incorporated herein by reference.

In one arrangement, the lead system 106B (as well as extension 106A where provided) may comprise a lead body of insulative material encapsulating a plurality of conductors within the material that extend from a proximal end (that is proximate to IPG 102) to the distal end of the lead body containing the lead electrodes 104-1 to 104-N. The conductors or conductive traces are operative to electrically couple the lead electrodes 104-1 to 104-N to a corresponding plurality of terminals (not shown) of the lead system 106A/B. In general, the terminals are adapted to receive electrical pulses from the pulse generation and switching circuitry of IPG 102, which are propagated via the corresponding conductive traces to at least a portion of the lead electrodes 104-1 to 104-N that are adapted to apply the pulses to a desired stimulation target of the patient depending on the particular stimulation therapy application. Also, sensing of physiological or bioelectrical signals may occur through a select number of lead electrodes 104-1 to 104-N, corresponding conductors, and associated terminals. By way of illustration, an example embodiment of the stimulation system 100A may be provided with a plurality of lead electrodes 104-1 to 104-N comprising four electrodes, eight electrodes, etc., although any suitable number of electrodes (as well as corresponding conductive traces and terminals) may be provided in a lead system. Additionally or alternatively, various sensors (e.g., a position detector, temperature sensor, one or more electrochemical sensors, a radiopaque fiducial, etc.) may be located near the distal end of the lead 106B and electrically coupled to terminals through associated conductors within the lead body.

Although not required for all embodiments, the lead body of the implantable lead system 106A/106B may be fabricated to flex and elongate upon implantation or advancing within or relative to the tissue (e.g., nervous tissue) of the patient towards the stimulation target to account for movement of the patient during or after implantation. Fabrication techniques and material characteristics for "body compliant" leads are disclosed in greater detail in U.S. Pat. No. 9,844,661, entitled "COMPLIANT ELECTRICAL STIMULATION LEADS AND METHODS OF FABRICATION", which is incorporated herein by reference.

An example implementation of the components within IPG 102, such as, e.g., processor and associated charge control circuitry for an IPG, is described in U.S. Pat. No. 7,571,007, entitled "SYSTEMS AND METHODS FOR USE IN PULSE GENERATION", which is incorporated herein by reference. An example implementation of circuitry for recharging a rechargeable battery (e.g., battery charging circuitry 122) of an IPG using inductive coupling and external charging circuits is described in U.S. Pat. No. 7,212,110, entitled "IMPLANTABLE DEVICE AND SYSTEM FOR WIRELESS COMMUNICATION", which is incorporated herein by reference. Still further, an example implementation of "constant current" pulse generating circuitry (e.g., at least a portion of pulse generating circuitry 110) is provided in U.S. Patent Application Publication No. 2006/0170486 entitled "PULSE GENERATOR HAVING AN EFFICIENT FRACTIONAL VOLTAGE CONVERTER AND METHOD OF USE", which is incorporated herein by reference. One or multiple sets of such circuitry may be provided within IPG 102 operating in association with a current control module for providing stimulation across a select number of electrodes. Different stimulation pulses on different lead electrodes selected from electrodes 104-1 to 104-N may be generated using consecutively generated pulses according to a "multi-stimset program" as is known in the art. Complex pulse parameters may be employed such as those described in U.S. Pat. No. 7,228,179, entitled "METHOD AND APPARATUS FOR PROVIDING COMPLEX TISSUE STIMULATION PATTERNS", and International Patent Publication Number WO 2001/093953, entitled "NEUROMODULATION THERAPY SYSTEM", which are incorporated herein by reference. Alternatively, multiple sets of such stimulation circuitry may be employed to provide high frequency pulse patterns (e.g., tonic stimulation waveform, burst stimulation waveform, and the like) that include generated and delivered stimulation therapy through one or more leads 104-1 to 104-N as is also known in the art. Various sets of parameters may define the pulse characteristics and pulse timing for the pulses applied to the various lead electrodes as is known in the art. Although constant current pulse generating circuitry is contemplated for some embodiments, any other suitable type of pulse generating circuitry may be employed such as constant voltage pulse generating circuitry.

In an example implementation of IPG 102, sensing circuitry 126 may be provided, preferably adapted to measure a suitable electric parameter or transduced characteristic (e.g., voltage, current, capacitance, etc.) over a configurable time associated with the stimulation target or tissue through at least one of the electrodes proximate to the stimulation target, e.g., electrodes configured to operate as biosensing inputs, wherein such "sensing" electrodes may be coupled to the sensing circuitry 126 via suitable alternating current (AC)-coupling capacitors. In an example embodiment, the sensing circuitry 126 may measure an evoked compound activation potential (ECAP) waveform from an Aβ sensory fiber or spinal cord. Optionally, the sensing circuitry 126 may store the measured/sensed electric data in memory 114. Furthermore, the diagnostic circuitry 111 may be configured to interoperate with the sensing circuitry 126 and pulse generation and switching functionalities of the IPG device 102 for effectuating diagnostic voltage/charge state measurements of one or more stimulated electrodes of the implanted lead system, which will be set forth further below in additional detail.

An external device 130 may be implemented to charge/recharge the battery 118 of IPG 102 (although a separate recharging device could alternatively be employed), to access memory 114, and/or to program or reprogram IPG 102 with respect to the stimulation set parameters including pulsing specifications, ramping sequences, etc., while implanted within the patient. In alternative embodiments, however, separate programmer devices may be employed for charging and/or programming the IPG 102 device and/or any programmable components thereof. An example embodiment of the external device 130 may be a processor-based system that possesses wireline and/or wireless communication capabilities, e.g., a tablet, smartphone, laptop computer, handheld computer, a personal digital assistant (PDA), or any smart wearable device and smart digital assistant device, etc. Software may be stored within a non-transitory memory of the external device 130, which may be executed by the processor to control the various operations of the external device 130. A connector or "wand" 134 may be electrically coupled to the external device 130 through suitable electrical connectors (not specifically shown), which may be electrically connected to a telemetry component 132 (e.g., inductor coil, RF transceiver, etc.) at the distal end of wand 134 through respective communication links that allow bi-directional communication with IPG 102. Optionally, in some embodiments, the wand 134 may comprise one or more temperature sensors for use during charging operations.

In one general scenario, a user (e.g., a doctor, a medical technician, or the patient) may initiate communication with IPG 102 by placing the wand 134 proximate to the stimulation system 100A. Preferably, the placement of the wand 134 allows the telemetry system to be aligned with the far-field and/or near field communication circuitry 124 of IPG 102. The external device 130 preferably provides one or more user interfaces 136 (e.g., touch screen, keyboard, mouse, buttons, scroll wheels or rollers, or the like), allowing the user to operate IPG 102. The external device 130 may be controlled by the user through the user interface 136, allowing the user to interact with IPG 102, including, e.g., dynamically configuring electrodes for effectuating different Kelvin connection schemes, providing programmatic control for facilitating voltage measurements and extraction of charge state data associated with the electrodes based on applicable equivalent ETI circuit models, etc. as will be set forth further below. Further, the user interface 136 may permit the user to move electrical stimulation along and/or across one or more of the lead(s) 106A using different lead electrode combinations selected from electrodes 104-1 to 104-N, for example, as described in U.S. Patent Application Publication No. 2009/0326608, entitled "METHOD OF ELECTRICALLY STIMULATING TISSUE OF A PATIENT BY SHIFTING A LOCUS OF STIMULATION AND SYSTEM EMPLOYING THE SAME", which is incorporated herein by reference. Optionally, the user interface 136 may permit the user to designate which electrodes 104-1 to 104-N are to stimulate (e.g., emit current pulses, in an anode state or in a cathode state), or not selected to stimulate (i.e., remain inactive or floating, i.e., "unused"), with respect to a potential stimulation target, to measure/sense tissue electrical parameters, or the like. As used herein, "stimulation" refers to the application of an electrical signal to a target body tissue, regardless of the effect that signal is intended to produce. Additionally or alternatively, the external device 130 may access or download the electrical measurements from the memory 114 acquired by the sensing circuitry 126 and/or diagnostic circuitry 111.

In some implementations, the external device 130 may permit operation of IPG 102 according to one or more spinal cord stimulation (SCS) programs or therapy applications to treat the patient. Each SCS program may include one or more sets of stimulation parameters of the pulse including pulse amplitude, stimulation level, pulse width, pulse frequency or inter-pulse period, pulse repetition parameter (e.g., number of times for a given pulse to be repeated for respective stimulation sets or stimsets during execution of program), biphasic pulses, monophasic pulses, etc. IPG 102 modifies its internal parameters in response to the control signals from the external device 130 to vary the stimulation characteristics of the stimulation therapy transmitted through the lead system 106A/106B to the tissue of the patient. Example neurostimulation (NS) systems, stimsets, and multi-stimset programs are set forth in U.S. Pat. No. 7,228,179, entitled "METHOD AND APPARATUS FOR PROVIDING COMPLEX TISSUE STIMULATION PATTERNS", and International Patent Publication Number WO 2001/093953, entitled "NEUROMODULATION THERAPY SYSTEM", which are incorporated hereinabove by reference.

It will be appreciated that although example lead system 106A/B shown in FIG. 1A is illustrated with a single implantable lead, the teachings herein are not necessarily limited thereto and an example embodiment of the present invention may involve a lead system comprising two or more implantable leads, which may comprise various types of leads such as paddle leads, percutaneous leads, etc., with each lead having a respective plurality of electrodes, wherein different types of Kelvin connection paths may implemented across a given equivalent ETI circuit model for measuring voltages/charge states in accordance with the teachings herein.

It is known that in providing a stimulation signal to a target body tissue, an accumulation of continuous or net charge at the electrode/tissue interface may occur, resulting in a residual voltage, which may not only dynamically affect the electrical characteristics of stimulation pulses being applied but also contribute to deterioration of lead electrode integrity. To maintain charge balance, accordingly, some arrangements of IPG 102 may include output coupling capacitors between the output circuits of the pulse generation/switching circuitry and the electrodes to block errant continuous direct current (DC) for the electrical signals being applied to the tissue. In such arrangements, charge built up on the electrodes during stimulation may be offset by use of such output coupling capacitors (DC blocking stimulation capacitors), and may be discharged when delivery of a portion of the electrical signal is completed, e.g., typically after delivery of an individual pulse in a stimulation signal. A "discharge phase" may be observed for a period, for example, after a monophasic stimulation phase. In one arrangement, the stimulation phase and the discharge phase taken together may be considered a charge-balanced pulse in a signal comprising a plurality of such pulses. Even in such arrangements, however, there may be a gradual buildup of residual voltage across the DC blocking stimulation capacitors over time, depending on the frequency and type of pulsing schemes and associated stimsets used, in addition to the charge/voltage buildup at the ETI of an implantable lead system.

Figure 1B:
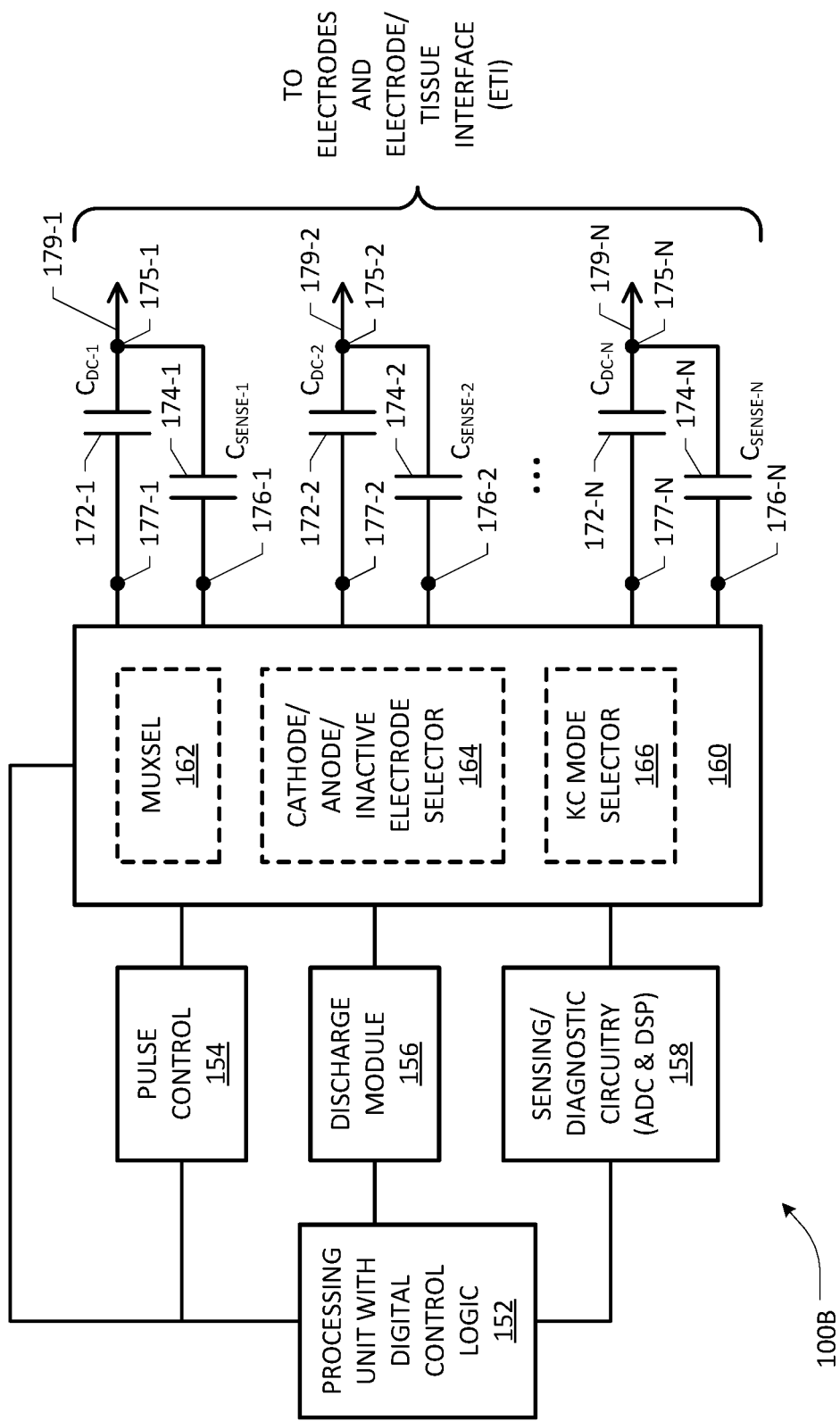
FIG. 1B depicts a pulse generator portion having diagnostic circuitry and associated lead electrode capacitor arrangement for purposes of an embodiment of the present disclosure.

Turning to FIG. 1B, depicted therein is a pulse generator portion 100B having diagnostic circuitry and associated lead electrode capacitor arrangement for purposes of an embodiment of the present disclosure. One skilled in the art will recognize upon reference hereto that various functionalities associated with example blocks shown as part of the pulse generator portion 100B may be distributed, integrated and/or otherwise (re)arranged among one or more blocks, subsystems and/or modules described hereinabove with respect to FIG. 1A. Consistent with the description set forth previously, a processing unit 152 having or associated with suitable digital control logic is operatively coupled to pulse control module 154, discharge module 156 and sensing/diagnostic circuitry 158 for facilitating various functionalities including but not limited to voltage measurements, active discharge cycling, electrode selection and configuration, etc., as well as charge state monitoring of an equivalent ETI circuit arrangement associated with a lead system under appropriate programmatic control. An input/output (I/O) interface block 160 is operatively coupled to a plurality of lead connectors 179-1 to 179-N comprising a lead system interfaced with respective electrodes and associated ETI that may be represented as circuitry based on known or heretofore unknown charge-transfer mechanisms or models (not shown in this FIG.). Each lead connector 179-1 to 179-N may be provided with a DC blocking stimulation capacitor ($C_{DC}$) for facilitating direct current flow blocking functionality with respect to the corresponding electrode that may be configured to operate as a stimulation node. In some embodiments, an AC-coupling sense capacitor ($C_{SENSE}$) may be optionally provided for facilitating AC-coupling functionality with respect to an electrode that may be configured to operate as a stimulation node or a sensing node. By way of illustration, DC blocking stimulation capacitor $C_{DC-1}$ 172-1 and sense capacitor $C_{SENSE-1}$ 174-1 are coupled to lead connector 179-1 such that two interface terminals 177-1 and 176-1 are effectuated with respect to the lead circuitry of the interface block 160. Sense capacitor $C_{SENSE-1}$ 174-1 is configured with $C_{DC-1}$ 172-1 such that an intermediate tap or node 175-1 is effectuated on the lead connector 179-1. Likewise, remaining lead connectors 179-N may be provided with respective $C_{SENSE-N}$ capacitors 174-N configured with corresponding $C_{DC-N}$ capacitors 172-N to facilitate two interface terminals or nodes 177-N and 176-N for each corresponding lead electrode connector. As will be seen below, such an arrangement facilitates a Kelvin connection path via the sense capacitor interface terminal 176-N with respect to each active electrode for purposes of voltage/charge state measurement and monitoring. Although the illustrated embodiment of FIG. 1B exemplifies an arrangement where each lead connector is provided with a corresponding sense capacitor, it should be appreciated that other arrangements may be realized within the scope of the present patent disclosure where not all lead connectors are coupled to and/or provided with respective sense capacitors.

Interface block 160 may include appropriate multiplexing and selection circuitry 162, anode/cathode/inactive electrode selection circuitry 164 and Kelvin connection (KC) mode selection circuitry 166 for effectuating various types of Kelvin connection schemes for measurement purposes while different electrodes of a lead system may be selectively configured for stimulation (e.g., anodic or cathodic stimulation), sensing, or designating unused/inactive states, etc., with appropriate electrical connections being made within an IPG device accordingly relative to the various components therein, under suitable programmatic control as needed. Example diagnostic circuitry 158 may comprise suitable analog-to-digital converter (ADC) circuitry configured for digitally-represented voltage measurements and associated signal processing using known or novel numerical computation techniques. As such, voltage measurement circuitry can be external and/or internal, on-board or off-board, and/or may be coupled to other measurement devices. Responsive to residual voltage measurements, active charge balancing may be effectuated in some example embodiments by applying a discharge pulse of opposite polarity at a select electrode to reduce or eliminate the individual residual voltages of select electrodes by using discharge cycle module 156 in conjunction with switch circuitry under suitable programmatic control. Additional details regarding configuring lead electrodes as cathodes or anodes, either during stimulation or for discharging, may be found in may be found in U.S. Patent Application Publication No. 2009/0048643, entitled "METHOD FOR PROVIDING MULTIPLE VOLTAGE LEVELS DURING PULSE GENERATION AND IMPLANTABLE PULSE GENERATING EMPLOYING THE SAME", which is hereby incorporated herein by reference.

Figure 1C:
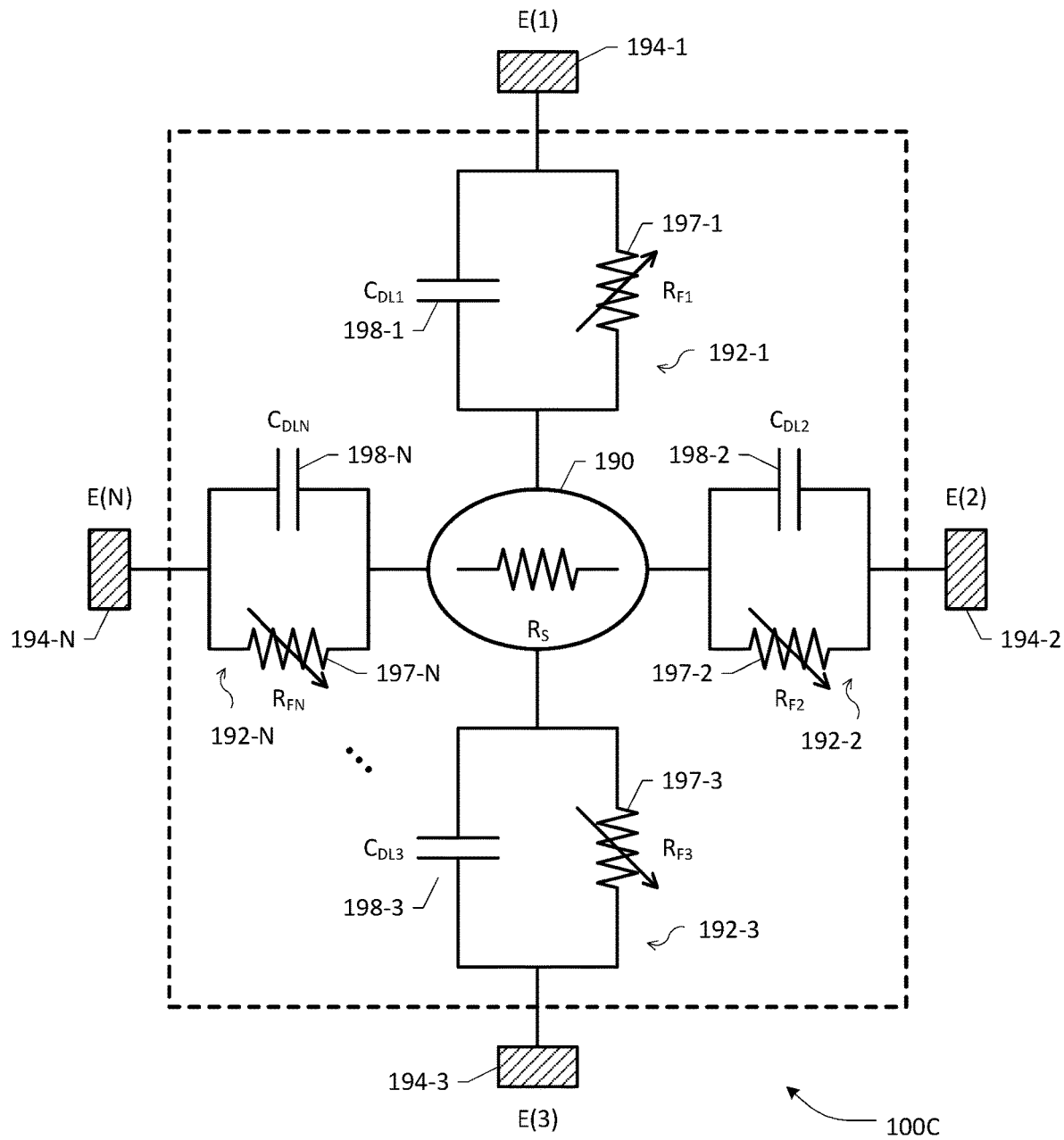
FIG. 1C depicts a generalized electrode/tissue interface (ETI) equivalent circuit arrangement for an IMD's lead electrode system wherein charge states associated with one or more capacitive components corresponding to individual electrodes may be evaluated using diagnostic circuitry according to an embodiment of the present disclosure.

When an electrode is placed near tissue, current flow is determined by the flow of electrons in the electrode and flow of ions in the tissue. The electrode/electrolyte (i.e., tissue) interface (EEI or ETI; also sometimes referred to as electrode/patient interface or EPI) is typically modeled in accordance with a linear lumped element charge transfer model (e.g., Randles equivalent circuit of the electrode-electrolyte interface), involving a series of lumped resistor elements coupled with a shunt capacitance that models the double layer of charge at the interface. FIG. 1C depicts a generalized ETI equivalent circuit arrangement 100C for an IMD's lead electrode system wherein the charge states of appropriate capacitive components associated with individual electrodes may be monitored, measured or otherwise characterized according to an embodiment of the present disclosure. In the illustrated arrangement 100C, the solution resistance, $R_S$, is representative of the bulk electrolyte, which models the tissue or patient resistance, $R_{PATIENT}$, as a pure resistive component 190 disposed across electrodes E(1) 194-1 to E(N) 194-N. With respect to each electrode, a double-layer capacitance or $C_{DL}$ models the double layer of charge at the interface, which is coupled in parallel to a charge transfer resistance $R_{CT}$, also referred to as Faradaic resistance ($R_F$), across the interface. Faradaic resistance, $R_F$, in parallel with the capacitance, $C_{DL}$, accounts for the conduction of charge through the interface, which can occur through various mechanisms, e.g., typically through oxidation-reduction reactions at the electrode for efficient operation of stimulation electrodes. Reference numerals 192-1 to 192-N shown in FIG. 1C accordingly refer to equivalent circuit representations of ETIs associated with corresponding electrodes 194-1 to 194-N, respectively, wherein $C_{DL1}$ 198-1 to $C_{DLN}$ 198-N and $R_{F1}$ 197-1 to $R_{FN}$ 197-N are illustrative of the respective lumped capacitive and resistive components thereof. Whereas more complex models of the electrode/tissue interface may be used, the foregoing charge transfer model is illustrated herein without necessarily being limited thereto for purposes of exemplifying how Kelvin connection paths may be advantageously effectuated for monitoring the charge states of one or more capacitive components (e.g., $C_{DC}$, $C_{DL}$ or both) associated with the respective individual electrodes of a lead system. A "Kelvin connection" for purposes of the present patent disclosure is a circuit arrangement that allows avoiding voltage drops (thereby current flows) in circuit segments in a measurement or instrumentation circuit path that may interfere with or confound measurement variables. Example embodiments disclosed herein facilitate such connection arrangements by employing either unused DC blocking stimulation capacitor paths and/or AC-coupling sense capacitor paths associated with respective electrodes (shown in FIG. 1B) in a variety of schemes or combinations (collectively, "modes") that may be selectively configured depending on a particular implementation in order to isolate the respective capacitive components of an electrode (e.g., depending on whether DC blocking capacitors ($C_{DC}$) are used in a voltage measurement path).

Figure 2A:
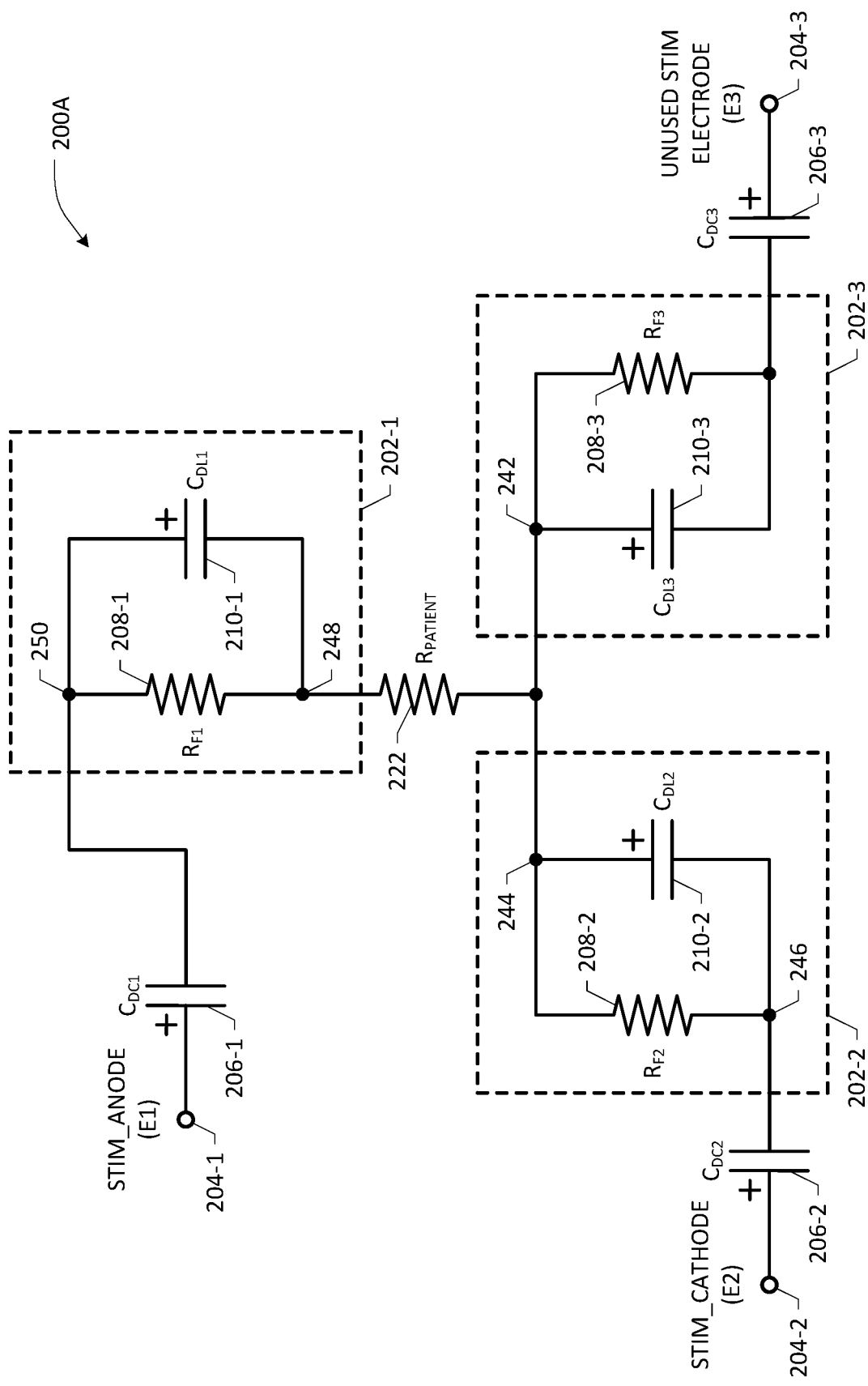
FIG. 2A depicts an example equivalent ETI circuit diagram for facilitating electrode charge state measurements in a sample electrode system using one type of Kelvin connection path according to an embodiment of the present disclosure.

FIG. 2A depicts an example equivalent ETI circuit diagram 200A configured for facilitating charge state measurements of capacitive components in a sample electrode system using one type of Kelvin connection path for purposes of an embodiment of the present disclosure. Three electrodes (E1, E2 and E3) and respective tissue interfaces 202-1 to 202-3 are shown by way of example. Illustratively, electrodes E1 and E2 are configured as stimulation anode and cathode, respectively, with electrode E3 being left unused or inactive. Each electrode is provided with a respective DC blocking stimulation capacitor $C_{DC}$, which facilitates a terminal or node with respect to an IPG interface block coupled to suitable diagnostic/sense circuitry as described previously. Further, each ETI 202-1 to 202-3 is exemplified by a corresponding $C_{DL}$ 210-1 to 210-3 coupled in parallel to respective charge transfer resistance $R_F$ 208-1 to 208-3, that is in series connection with the bulk patient resistance $R_{PATIENT}$ 222 effectively disposed between a pair of the electrodes in any applicable combination. Because E3 is configured as an unused electrode for stimulation, its DC blocking stimulation capacitor $C_{DC3}$ 206-3 is kept in a discharged state, which allows the associated terminal 204-3 to be used in a Kelvin connection path with respect to other electrode terminals in a measurement circuit loop. For example, a measurement loop between terminal 204-2 of cathode-active electrode E2 and terminal 204-3 of unused electrode E3 can be used to measure a voltage comprising a sum of a voltage across $C_{DC2}$ 206-2 and a voltage across $C_{DL2}$ 210-2 because terminal 204-3 is at the same level as internal nodes 242 and 244 of the circuit arrangement 200A. Accordingly, the measured voltage is indicative of the total charge state across the DC blocking capacitance ($C_{DC2}$) and the double-layer ETI capacitance ($C_{DL2}$) components associated with electrode E2 204-2. In a typical DBS implementation where $C_{DC}$ capacitances are substantially larger than the $C_{DL}$ capacitances (e.g., by one or more orders of magnitude), the charge state or buildup on the DC blocking stimulation capacitors may be small enough that it may be ignored in estimating the voltage measurement across $C_{DL}$ associated with the selected active electrode, e.g., E2. In such a scenario, the voltage measurement may therefore be treated as being sufficiently close to the voltage component due to the charge state associated with $C_{DL2}$ 210-2. On the other hand, in typical SCS implementations, the differences between $C_{DL}$ and $C_{DC}$ capacitances are usually less than one order of magnitude (e.g., around seven times). Accordingly, in such an application, the charge state on SCS DC blocking stimulation capacitors ($C_{DC}$) cannot be ignored as readily for purposes of obtaining $C_{DL}$ charge states in the embodiment shown in FIG. 2A.

In similar fashion, a voltage measurement loop between terminal 204-1 of electrode E1 (configured as an anode stimulation node) and terminal 204-3 of unused electrode E3 can be effectuated in order obtain a charge state measurement associated with E1. Such a measurement may include a component representing voltage buildup during stimulation across $C_{DC1}$ 206-1 and voltage buildup across $C_{DL1}$ 210-1 since terminal 204-3 is at the same voltage level as internal nodes 242 and 248 (because outside of stimulation there is little current flow in the inactive electrode path through the bulk tissue resistance $R_{PATIENT}$ 222; however, the inactive electrode is most generally used as a Kelvin connection only when there is no stimulation nor discharge current flowing through the patient/tissue, although there can be exceptions). Further, the voltage measurement may be treated as a reasonable approximation of the charge state buildup after stimulation across $C_{DL1}$ 210-1 since $C_{DC1}$ 206-1 is typically much larger than $C_{DL1}$ 210-1 in certain applications, as noted previously. An example implementation of the circuit arrangement 200A may comprise $C_{DC}$ capacitances around 20-30 μF whereas the $C_{DL}$ capacitances may be around 0.1-3.0 μF. Skilled artisans will also recognize that the $C_{DC}$ capacitance values may be even lower, e.g., around 10-15 μF, especially in smaller physical form factor implementations. Where the $C_{DC}$ capacitance cannot be ignored, however, a total or composite charge state associated with the $C_{DC}$ capacitance and the $C_{DL}$ capacitance of a stimulation electrode involved in the Kelvin voltage measurement path may be obtained.

Accordingly, a Kelvin connection path effectuated via the $C_{DC}$ terminal of an inactive electrode of an implantable lead system as set forth above may be used in some embodiments for obtaining charge state measurements associated with the capacitive components of respective active electrodes of the lead system. As will be set forth further below, a switching circuit may be provided in order to appropriately/selectively connect different Kelvin connection paths, each referencing to the $C_{DC}$ terminal of an inactive electrode (referred to herein as a "Kelvin electrode" in some embodiments), across a sense input and a reference input of an ADC provided as part of a diagnostic circuit that may be configured to generate a suitable N-bit digitally-represented voltage measurement.

Skilled artisans will recognize that in an embodiment utilizing the above Kelvin connection scheme, the charge states associated with the $C_{DC}$ capacitor component as well as the $C_{DL}$ capacitor component of an electrode are typically included together in a measurement unless the effect of the $C_{DC}$ capacitor component may reasonably be neglected. To facilitate the separation of the charge states of $C_{DC}$ and $C_{DL}$ capacitor components in a measurement loop, an AC-coupling sense capacitor path of an active electrode may be used in a further embodiment as a Kelvin connection path at the other end of the measurement loop in conjunction with a Kelvin connection path at an inactive electrode as set forth above (i.e., using a Kelvin electrode connection). In still further embodiments, an inactive electrode may also be provided with an AC-coupling sense capacitor path (which is a likely implementation scenario since it is preferable to manufacture identical electrodes in a lead system that can be selectively and dynamically configured depending on a particular stimulation application and associated stimset variations). In such embodiments, an alternative Kelvin connection path may be established at the inactive electrode in addition to the inactive DC blocking stimulation $C_{DC}$ capacitor path thereat. One skilled in the art will therefore readily appreciate that a number of Kelvin connection modes may be effectuated in an example IMD/IPG system depending on the various AC-coupling and/or DC blocking stimulation capacitor arrangements provided with respect to the electrodes of a lead system and/or how the different electrodes and corresponding capacitor arrangements are selectively configured. For example, where a subset of the electrodes are configured to be active, the remaining electrodes (one or more of the rest of the electrodes) may be disposed as inactive electrodes, out of which any one particular electrode may be configured as one end of a Kelvin connection path with respect to a voltage/charge state measurement loop. Such a Kelvin connection path may be effectuated via the selected inactive node's DC blocking stimulation capacitor path or via its AC-coupling sense capacitor path, as noted above. In an additional/alternative embodiment, one of the electrodes of a lead system may be designated or dedicated to operate as a Kelvin connection terminal that may be selectively and switchably connected with an ADC-based diagnostic circuit for effectuating voltage/charge measurements with respect to any one or combination of the active electrodes of the lead system for purposes of the present patent disclosure.

Figure 2B:
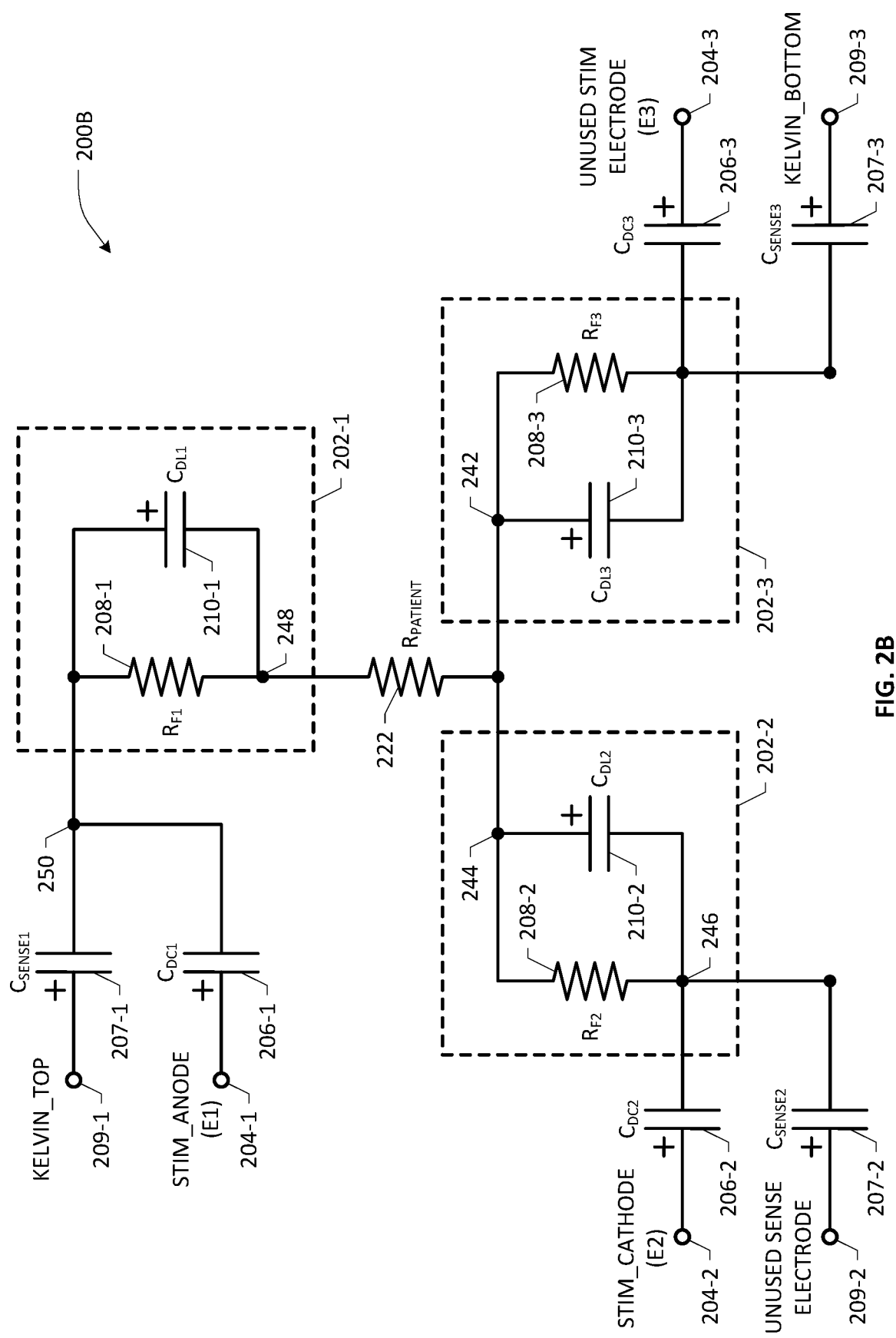
FIG. 2B depicts an example equivalent ETI circuit diagram for facilitating electrode charge state measurements in a sample electrode system using a combination of Kelvin connection paths according to another embodiment of the present disclosure.

Turning to FIG. 2B, depicted therein is an example equivalent ETI circuit diagram 200B that may be configured to illustrate one or more of the foregoing embodiments for facilitating charge state measurements of different capacitive components of a sample lead system using different types and/or combinations of Kelvin connection paths according to the present patent disclosure. Similar to the arrangement 200A illustrated in FIG. 2A, circuit arrangement 200B of FIG. 2B exemplifies three electrodes, E1-E3, each shown with corresponding ETI circuit representations 202-1 to 202-3 coupled to bulk patient resistance $R_{PATIENT}$ 222 in a "star" configuration. Further, electrodes E1 and E2 are illustrated as active stimulation nodes while electrode E3 is left as an inactive/unused electrode as before. Each electrode is provided with corresponding biosensing input terminal 209-1 to 209-3, effectuated via respective AC-coupling capacitors $C_{SENSE1}$ 207-1 to $C_{SENSE3}$ 207-3 that are coupled in parallel to the respective DC-blocking capacitors, $C_{DC1}$ 206-1 to $C_{DC3}$ 206-3. In one embodiment, the AC-coupling capacitors $C_{SENSE1}$ 207-1 to $C_{SENSE3}$ 207-3 may be implemented as low capacitance components (e.g., around 0.1 µF), which may be maintained to be readily kept in a discharged state (e.g., because no stimulation current will flow through such capacitors). Accordingly, voltage levels at the AC-coupling capacitors $C_{SENSE1}$ 207-1 to $C_{SENSE3}$ 207-3 of electrodes E1-E3 are near or close to 0 V (or some other reference potential), which can facilitate respective Kelvin connection paths for measuring the voltages in connection with a select charge state measurement loop depending on which electrode's voltage is being measured. For example, terminal 209-1 associated with $C_{SENSE1}$ 207-1 may be deemed a "Kelvin_Top" terminal or node which is at the same potential as internal node 250 with respect to ETI 202-1 of electrode E1. By utilizing terminal 209-3 associated with $C_{SENSE3}$ 207-3 of the unused electrode E3 as a "Kelvin_Bottom" terminal (which is at the same potential as internal node 242), a voltage measurement across $C_{DL1}$ 210-1 may be obtained in a manner similar to the voltage measurement process discussed above. Further, the $C_{DC3}$ terminal 204-3 of the unused electrode E3 may also be used in conjunction with terminal 209-1 operating as the "Kelvin_Top" terminal in an alternative embodiment, as previously described. Skilled artisans will recognize this alternative Kelvin connection path may be beneficial to use if the biosensing AC-coupling $C_{SENSE3}$ 207-3 terminal 209-3 associated with electrode E3 is already in use for biosensing and it is required that the sensing activity from electrode E3 remain undisturbed. Likewise, voltage/charge state at other active electrodes (i.e., across respective $C_{DL}$ capacitances) may be measured by using corresponding $C_{SENSE}$ terminals in conjunction with either of the Kelvin connection paths available at the unused electrode E3 in a similar manner.

In one example scenario, if voltage measurements are taken using a Kelvin connection path between node 209-1 and node 204-3 or node 209-3, $C_{DC1}$ 206-1 is not in a series combination with $C_{DL1}$ 210-1, and hence only the charge state associated with the double-layer capacitance of the equivalent ETI circuit of E1 electrode may be measured, monitored, or otherwise characterized. On the other hand, if node 204-1 of the DC capacitance associated with E1 electrode is utilized for taking voltage measurements with respect to either node 204-3 or node 209-3, $C_{DC1}$ 206-1 is included in a series combination with $C_{DL1}$ 210-1, and hence a total charge state associated with both $C_{DC1}$ 206-1 and $C_{DL1}$ 210-1 may be obtained. In one example embodiment, by switchably connecting either node 209-1 or node 204-1 to a sense input of the ADC diagnostic circuit, each of which may be disposed in a Kelvin connection path, e.g., with either node 204-3 or 209-3 that may also be switchably connected to a reference input of the ADC diagnostic circuit (not shown in this FIG.), individual charge states associated with $C_{DC1}$ 206-1, $C_{DL1}$ 210-1, or both, may be obtained. In one example implementation, the charge state of $C_{DC1}$ 206-1 may be obtained as a difference between the total charge state and the charge state associated with $C_{DL1}$ 210-1. Likewise, different Kelvin connection paths involving electrical nodes associated with cathodic E2 electrode and electrical nodes associated with the unused E3 electrode may be used for obtaining voltage measurements with respect to $C_{DC2}$ 206-2, $C_{DL2}$ 210-2, and/or both capacitances of the corresponding ETI circuit arrangement associated with E2 electrode.

Whereas example Kelvin connection paths illustrated above involve a pair of electrodes across the EPI/ETI interface with suitable capacitor terminals operating as Kelvin connection terminals, additional and/or alternative embodiments according to the teachings of the present invention may also involve any combination of any subset of the active electrodes and any subset of the unused/inactive electrodes in a Kelvin connection path on the either side of the EPI interface for obtaining voltage measurements, with appropriate capacitor terminal connections as described herein, mutatis mutandis, for obtaining charge states associated with different portions of an IPG lead system. Additional details regarding implementing Kelvin connections in an IPG and associated lead systems comprising one or more leads may be found in U.S. patent application Ser. No. 16/195,502, filed Nov. 19, 2018, entitled, "KELVIN CONNECTION SCHEME FOR DIAGNOSTIC CAPABILITY IN A NEUROSTIMULATOR", which is incorporated by reference herein.

Figure 3:
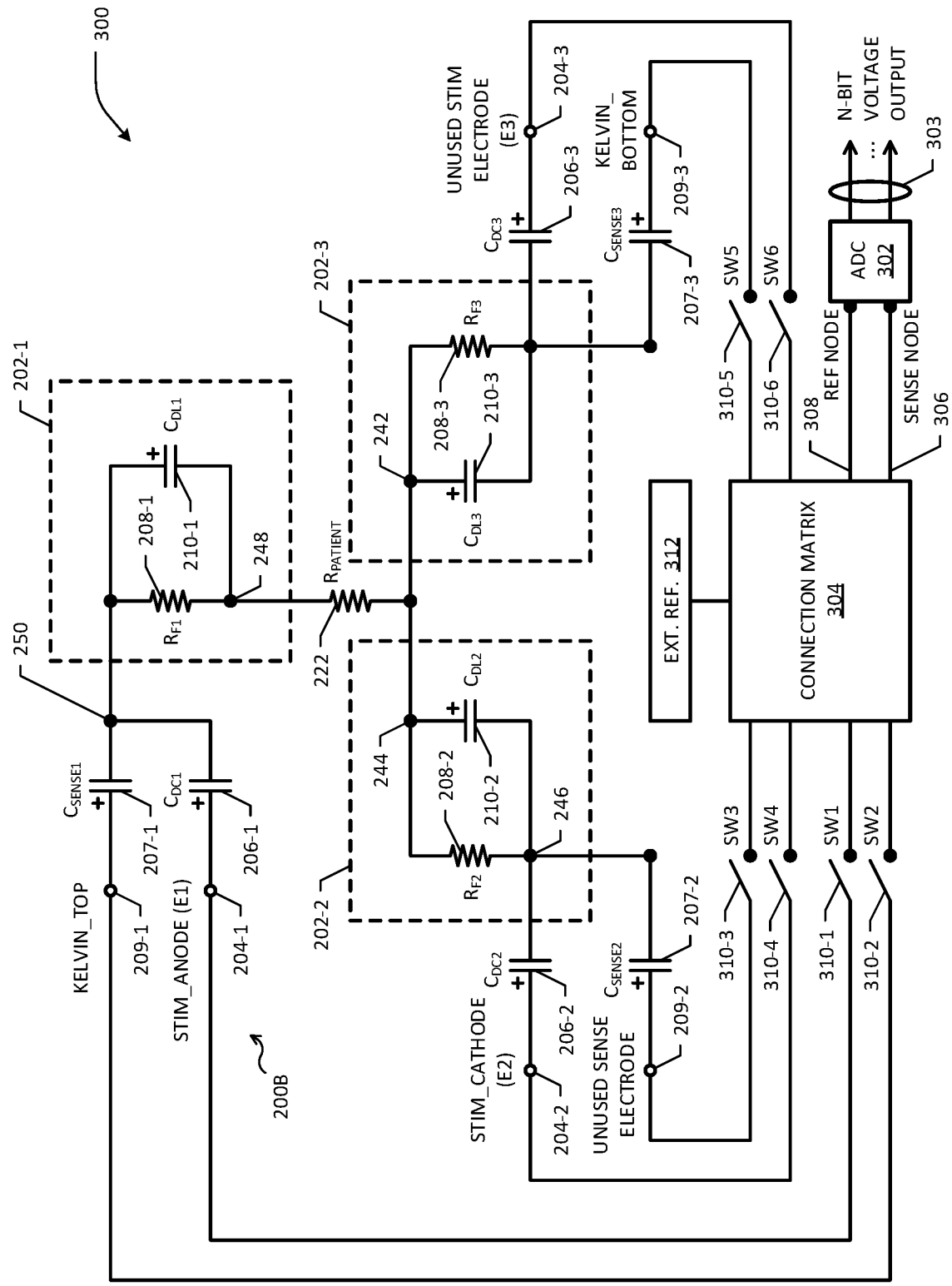
FIG. 3 depicts an example diagnostic circuit arrangement operative with a plurality of switches and associated connection matrix for facilitating measurement and monitoring of voltages/charge states using a combination of Kelvin connection paths involving different capacitive components of the sample electrode system shown in FIG. 2B.
Figure 4A:
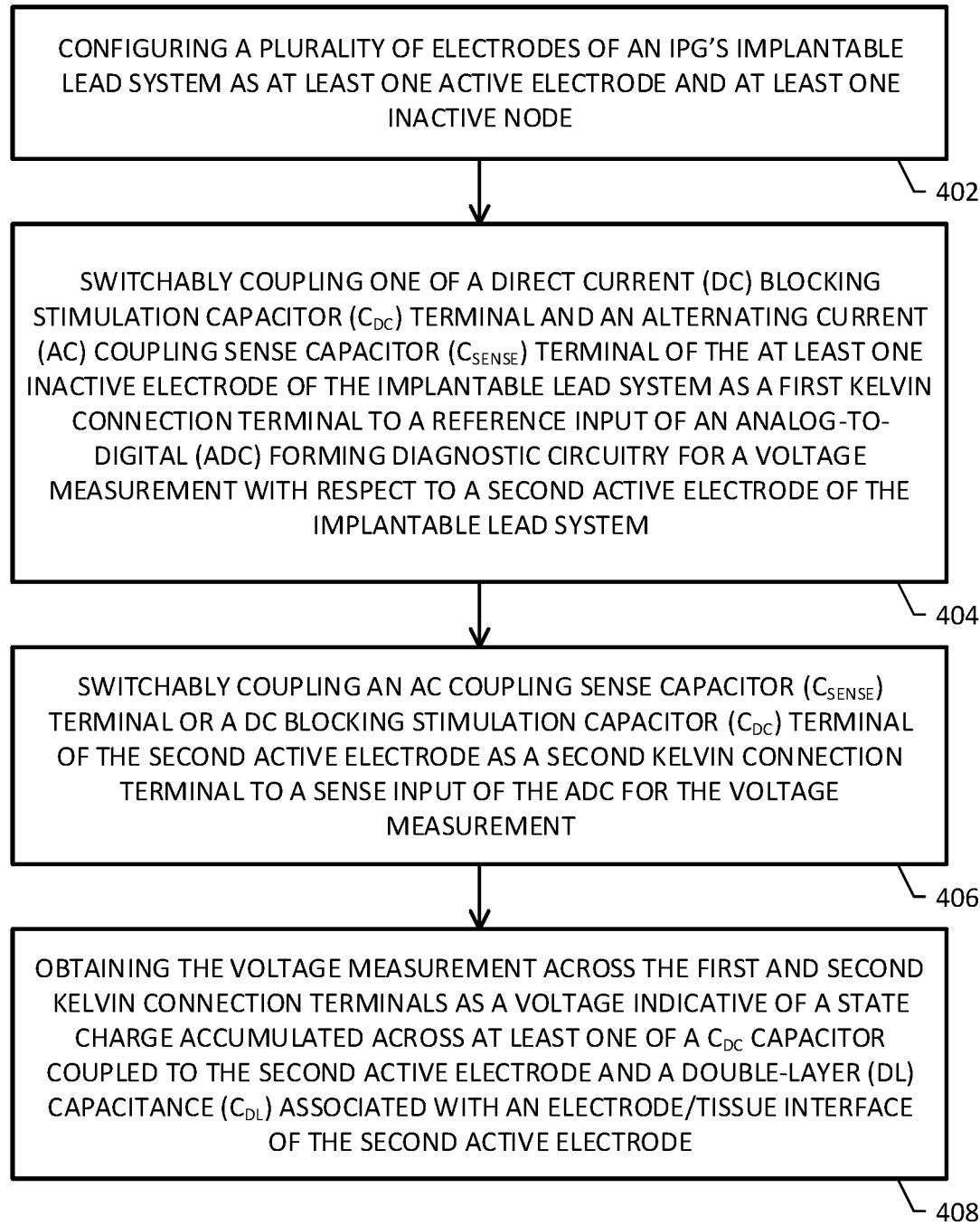

FIG. 3 depicts an example diagnostic circuit arrangement 300 including a plurality of switches and associated switching connection matrix for facilitating measurements of voltages/charge states of electrode capacitances using a variety of selectively switchable Kelvin connection paths involving different capacitive components of the sample electrode system 200B shown in FIG. 2B. In one embodiment, a plurality of switches SW1 310-1 to SW6 310-6 may be provided with respect to a corresponding plurality of connections disposed between the terminals of the electrodes (active and unused) and a connection matrix 304 for connecting a Kelvin electrode terminal to a reference input node 308 and an individual stimulation electrode terminal (where the charge state is to be measured) to a sense input node 306 of an ADC 302. For example, if SW6 310-6 is ON such that the connection matrix 304 couples the unused and completely discharged Kelvin connect electrode terminal 204-3 of E3 to the reference input node 308 of ADC 302, and SW2 310-2 is ON such that Kelvin_Top terminal 209-1 associated with anode electrode E1 is coupled to the sense input node 306, the voltage and charge state of the $C_{Du}$ component 210-1 of the anodic electrode E1 may be monitored as set forth above, which may be converted to an N-bit digitally-represented voltage output 303. In one implementation of the foregoing arrangement, it should be noted that all other switches are turned OFF, i.e., not connected to the reference and sense input nodes 308, 306 of ADC 302. In similar fashion, the voltage and charge state of the cathodic electrode E2 (associated with $C_{DC2}$ and $C_{DL2}$ components) can be individually measured and monitored, e.g., when SW4 310-4 is ON such that it is coupled to the sense input node 306 of ADC 302 and either SW5 310-5 or SW6 310-6 is ON and selectively connected to the reference input node 306 of ADC 302. In a still further or alternative embodiment, a separate/external reference 312 having a known voltage state may be provided or otherwise coupled to the reference input node 308 of ADC 302 instead of a Kelvin electrode, unused sense terminal, or a dedicated electrode for purposes of facilitating voltage/charge state measurements by ADC 302.

Skilled artisans will recognize that the foregoing plurality of switches 310-1 to 310-6 and/or associated connection matrix 304 may be implemented or integrated in a number of arrangements using a variety of discrete and/or integrated electronic devices including but not limited to diodes, transistors, etc., wherein suitable control logic signals may be provided for actuating the switches/connection matrix in order to effectuate appropriate switchable connectivity between select electrode terminals and ADC terminals 306, 308, based on a selected Kelvin connection mode. In one implementation, such control logic signals may be generated or provided by an external programmer executing suitable program instructions responsive to user input. Further, a simplified switching arrangement, connection matrix circuitry and associated digital control logic may be implemented in conjunction with the Kelvin connection scheme involving the sample electrode system 200A shown in FIG. 2A, similar to the embodiment described above with respect to the Kelvin connection scheme of FIG. 2B, mutatis mutandis. In such an arrangement, however, the charge states associated with the $C_{DL}$ capacitances of individual ETIs may not be separately characterized due to the lack of $C_{SENSE}$ terminals as previously noted.

FIGS. 4A-4D depict flowcharts illustrative of blocks, steps and/or acts that may be (re)combined in one or more arrangements with or without other flowcharts for monitoring the charge states of an IPG/IMD lead system according to some embodiments of the present disclosure. In one embodiment, example process 400A of FIG. 4A may involve configuring a plurality of electrodes of an IPG/IMD's implantable lead system as having at least one active electrode and at least one inactive node with respect to providing a particular stimulation therapy (block 402). At block 404, one of a direct current (DC) blocking stimulation capacitor ($C_{DC}$) terminal or an alternating current (AC) coupling sense capacitor ($C_{SENSE}$) terminal of the at least one inactive electrode of the implantable lead system may be switchably coupled as a first Kelvin connection terminal to a reference input/node of an ADC forming diagnostic circuitry for facilitating a voltage measurement with respect to a second active electrode of the implantable lead system. At block 406, an AC coupling sense capacitor ($C_{SENSE}$) terminal or a DC blocking stimulation capacitor ($C_{DC}$) terminal of the second active electrode may be switchably coupled as a second Kelvin connection terminal to a sense input/node of the ADC for the voltage measurement. A digital output may be obtained as the representation of the voltage measurement across the first and second Kelvin connection terminals, which is indicative of a charge state accumulated across at least one of a $C_{DC}$ capacitor coupled to the second active electrode and a double-layer (DL) capacitance ($C_{DL}$) associated with an electrode/tissue interface of the second active electrode (block 408). In one embodiment, a Kelvin connection selection mode may be set/reset or otherwise selected to configure a plurality of switches in order to selectively effectuate different combinations of voltage measurement connection paths between the terminals of the electrodes and the sense and reference inputs of the ADC of the diagnostic circuitry, as set forth at block 420 of example process 400B of FIG. 4B. In one embodiment, at least one inactive electrode may be configured as a dedicated Kelvin electrode of the implantable lead system for facilitating at least one Kelvin connection path for measuring voltages respectively associated with one or more active electrodes of the implantable lead system, as set forth at block 430 of example process 400C of FIG. 4C. In one embodiment, at least one active electrode may be configured as one of a cathode to provide cathodic stimulation or an anode to provide anodic stimulation to a patient's tissue according to a particular therapy application, as set forth at block 440 of example process 400D of FIG. 4D. As is known in the art, such therapy applications may comprise a therapy selected from at least one of a spinal cord stimulation (SCS) therapy, a neuromuscular stimulation therapy, a dorsal root ganglion (DRG) stimulation therapy, a deep brain stimulation (DBS) therapy, a cochlear stimulation therapy, a cardiac pacemaker therapy, a cardioverter-defibrillator therapy, a cardiac rhythm management (CRM) therapy, an electrophysiology (EP) mapping and radio frequency (RF) ablation therapy, an electroconvulsive therapy (ECT), a repetitive transcranial magnetic stimulation (rTMS) therapy, and a vagal nerve stimulation (VNS) therapy.

Figure 5:
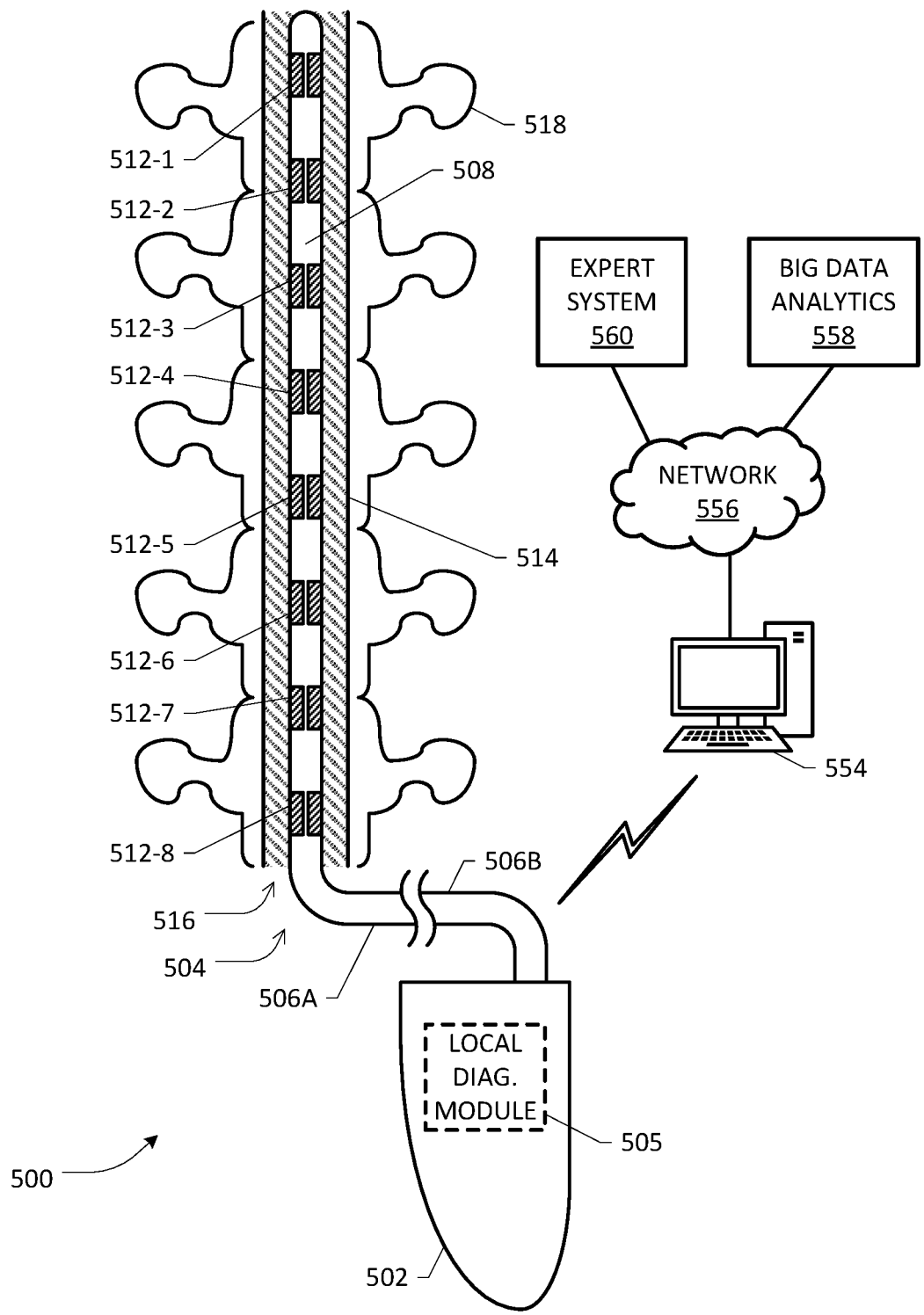
FIG. 5 illustrates an example spinal cord stimulation (SCS) therapy application involving an IPG/IMD and associated lead system having a plurality of electrodes wherein the charge states of different electrodes may be obtained using an embodiment of the present disclosure.

FIG. 5 illustrates an example spinal cord stimulation (SCS) therapy application 500 involving an IPG/IMD 502 and associated lead system 504 having a plurality of electrodes 512-1 to 512-8 wherein the charge states of different electrodes may be obtained using an embodiment of the present disclosure. Preferably, the lead system 504 comprises a lead body 506A/B coupled to an implantable lead 508 that may be positioned at a desired target position in an epidural space 516 defined by a plurality of vertebrae 518 of a patient so as to be in close proximity to a nerve tissue of interest, e.g., a spinal cord 514. Example lead 508 includes eight electrodes 512-1 to 512-8, which may comprise ring electrodes, segmented or split electrodes, etc. that may be separated from one another by equal or unequal portions of encapsulating material. The implantable lead 508 is connected via lead body 506A/506B to the pulse generator or IMD 502 that includes at least an embodiment of a Kelvin connection scheme configured to be operative with suitable diagnostic circuitry 505 of the present disclosure. At least a subset of the electrodes 512-1 to 512-8 may be selectively energized, i.e., stimulated to a target setting, according to a therapy program. At any desired time, voltage/charge state measurements may be taken by effectuating a switchable combination of Kelvin connections with respect to the electrodes in connection with the diagnostic circuitry 505. For example, in one embodiment electrodes 512-1, 512-4 and 512-8 may be programmed as cathodes or anodes for operation in conjunction with the case or can of the IPG/IMD 502 for providing current stimulation to effectuate an electric field that is spatially distributed over a target portion of the spinal cord 14. An unused electrode, e.g., electrode 512-5, may be used to establish a Kevin connection path on the inactive side of the measurement loop with respect to any of the selected active electrodes 512-1, 512-4 and 512-8 for measuring the voltages/charge states associated therewith.

Although a single implantable lead 508 is exemplified herein, it should be appreciated that a lead system comprising multiple leads, each having a corresponding plurality of electrodes, may be implemented in a stimulation therapy application, wherein appropriate Kelvin connection paths for each lead may be established for different subsets of active and unused electrodes therein across its corresponding electrode/patient interface.

In one example scenario, the diagnostic circuitry 505 of IPG/IMD 502 may therefore be configured to perform, under programmatic control, the following: utilize one of a direct current (DC) blocking stimulation capacitor ($C_{DC}$) terminal and an alternating current (AC) coupling sense capacitor ($C_{SENSE}$) terminal of an inactive electrode, e.g., electrode 512-5 of the implantable lead system 504 as a first Kelvin connection terminal for a voltage measurement with respect to a select active electrode, e.g., electrode 512-4, of the implantable lead system 504; utilize a terminal of an alternating current (AC) coupling sense capacitor ($C_{SENSE}$) coupled to the select active electrode 512-4 as a second Kelvin connection terminal for the voltage measurement; and selectively/switchably couple the first and second Kelvin connection terminals to a voltage measurement circuit in order to measure a voltage/charge state associated with the select active electrode in accordance with the teachings herein.

In a further arrangement, the measured voltages/charge state information of the electrodes may be transmitted via a suitable interface to an external node or device 554 (e.g., a clinician programmer, a patient controller, etc.) that may be configured to execute the ETI parametric extraction. In still further arrangements, external node 554 may be configured as a communication gateway operative to provide the measured voltage/charge state data and/or ETI parametric data over a network 556 to remote nodes such as expert systems 560, Big Data analytics 558, etc. to facilitate data mining, adaptive biostimulation therapy based on machine learning, artificial intelligence, and the like. Also, in still further embodiments, the charge state data and historical patterns associated therewith may be provided to facilitate improved manufacture/fabrication of electrodes, optimization of electrode performance, etc.

In the above-description of various embodiments of the present disclosure, it is to be understood that the terminology used herein is for the purpose of describing particular embodiments only and is not intended to be limiting of the invention. Unless otherwise defined, all terms (including technical and scientific terms) used herein have the same meaning as commonly understood by one of ordinary skill in the art to which this invention belongs. It will be further understood that terms, such as those defined in commonly used dictionaries, should be interpreted as having a meaning that is consistent with their meaning in the context of this specification and the relevant art and may not be interpreted in an idealized or overly formal sense expressly so defined herein.

At least some example embodiments are described herein with reference to one or more circuit diagrams/schematics, block diagrams and/or flowchart illustrations. It is understood that such diagrams and/or flowchart illustrations, and combinations of blocks in the block diagrams and/or flowchart illustrations, can be implemented by any appropriate circuitry configured to achieve the desired functionalities. Accordingly, example embodiments of the present disclosure may be embodied in hardware and/or in software (including firmware, resident software, micro-code, etc.) operating in conjunction with suitable processing units or microcontrollers, which may collectively be referred to as "circuitry," "a module" or variants thereof. An example processing unit or a module may include, by way of illustration, a general purpose processor, a special purpose processor, a conventional processor, a digital signal processor (DSP), a plurality of microprocessors, one or more microprocessors in association with a DSP core, a controller, a microcontroller, Application Specific Integrated Circuits (ASICs), Field Programmable Gate Array (FPGA) circuits, any other type of integrated circuit (IC), and/or a state machine, as well as programmable system devices (PSDs) employing system-on-chip (SoC) architectures that combine memory functions with programmable logic on a chip that is designed to work with a standard microcontroller. Example memory modules or storage circuitry may include volatile and/or nonvolatile memories such as, e.g., random access memory (RAM), electrically erasable/programmable read-only memories (EEPROMs) or UV-EPROMS, one-time programmable (OTP) memories, Flash memories, static RAM (SRAM), etc.

Further, in at least some additional or alternative implementations, the functions/acts described in the blocks may occur out of the order shown in the flowcharts. For example, two blocks shown in succession may in fact be executed substantially concurrently or the blocks may sometimes be executed in the reverse order, depending upon the functionality/acts involved. Moreover, the functionality of a given block of the flowcharts and/or block diagrams may be separated into multiple blocks and/or the functionality of two or more blocks of the flowcharts and/or block diagrams may be at least partially integrated. Furthermore, although some of the diagrams include arrows on communication paths to show a primary direction of communication, it is to be understood that communication may occur in the opposite direction relative to the depicted arrows. Finally, other blocks may be added/inserted between the blocks that are illustrated.

It should therefore be clearly understood that the order or sequence of the acts, steps, functions, components or blocks illustrated in any of the flowcharts depicted in the drawing Figures of the present disclosure may be modified, altered, replaced, customized or otherwise rearranged within a particular flowchart, including deletion or omission of a particular act, step, function, component or block. Moreover, the acts, steps, functions, components or blocks illustrated in a particular flowchart may be inter-mixed or otherwise inter-arranged or rearranged with the acts, steps, functions, components or blocks illustrated in another flowchart in order to effectuate additional variations, modifications and configurations with respect to one or more processes for purposes of practicing the teachings of the present patent disclosure.

Although various embodiments have been shown and described in detail, the claims are not limited to any particular embodiment or example. None of the above Detailed Description should be read as implying that any particular component, element, step, act, or function is essential such that it must be included in the scope of the claims. Where the phrases such as "at least one of A and B" or phrases of similar import are recited or described, such a phrase should be understood to mean "only A, only B, or both A and B." Reference to an element in the singular is not intended to mean "one and only one" unless explicitly so stated, but rather "one or more." Moreover, the terms "first," "second," and "third," etc. employed in reference to elements or features are used merely as labels, and are not intended to impose numerical requirements, sequential ordering or relative degree of significance or importance on their objects. All structural and functional equivalents to the elements of the above-described embodiments that are known to those of ordinary skill in the art are expressly incorporated herein by reference and are intended to be encompassed by the present claims. Accordingly, those skilled in the art will recognize that the exemplary embodiments described herein can be practiced with various modifications and alterations within the spirit and scope of the claims appended below.

The invention claimed is:

1. An implantable medical device, comprising:
a power supply module;
a processing unit;
a pulse generator;
an implantable lead system including at least one lead having a plurality of electrodes adapted to stimulate a patient's tissue responsive to instructions generated by the processing unit in association with the pulse generator, the plurality of electrodes including at least one inactive electrode and at least one active electrode;
electrode selection circuitry operative to configure each electrode of the at least one inactive electrode as not selected to stimulate with respect to the patient's tissue and to configure each electrode of the at least one active electrode as selected to stimulate with respect to the patient's tissue, wherein a first inactive electrode of the at least one inactive electrode is not selected to stimulate and thereby configured by the electrode selection circuitry as inactive and a second active electrode of the at least one active electrode is selected to stimulate and thereby configured by the electrode selection circuitry as active;
diagnostic circuitry comprising an analog-to-digital converter (ADC) having a sense input and a reference input; and
switching circuitry operative to selectively couple one or more terminals associated with each electrode to the ADC of the diagnostic circuitry, the switching circuitry including one or more switches for each electrode corresponding to the one or more terminals associated therewith,
wherein the diagnostic circuitry is configured to perform following acts in conjunction with the switching circuitry and the processing unit:
utilize a first direct current (DC) blocking stimulation capacitor ($C_{DC1}$) terminal coupled to the first inactive electrode or a first alternating current (AC) coupling sense capacitor ($C_{SENSE1}$) terminal coupled to the first inactive electrode as a first Kelvin connection terminal switchably coupled by the switching circuitry to the reference input of the ADC for a voltage measurement with respect to the second active electrode;
utilize a second AC coupling sense capacitor ($C_{SENSE2}$) terminal coupled to the second active electrode or a second DC blocking stimulation capacitor ($C_{DC2}$) terminal coupled to the second active electrode as a second Kelvin connection terminal switchably coupled by the switching circuitry to the sense input of the ADC for the voltage measurement; and
obtain the voltage measurement across the first and second Kelvin connection terminals as a voltage indicative of a charge state accumulated across at least one of a $C_{DC2}$ capacitor coupled to the $C_{DC2}$ terminal or a double-layer (DL) capacitance ($C_{DL}$) associated with an electrode/tissue interface (ETI) of the second active electrode.

2. The implantable medical device as recited in claim 1, further comprising a mode selector operative to configure the switching circuitry to effectuate different combinations of voltage measurement connection paths between the terminals of the electrodes and the sense and reference inputs of the ADC of the diagnostic circuitry.

3. The implantable medical device as recited in claim 2, wherein the at least one inactive electrode comprises a dedicated Kelvin electrode of the implantable lead system for facilitating at least one Kelvin connection path with respect to measuring voltages respectively associated with one or more active electrodes of the at least one active electrode of the implantable lead system.

4. The implantable medical device as recited in claim 2, wherein the second active electrode is configured as one of a cathode to provide cathodic stimulation to the patient's tissue and an anode to provide anodic stimulation to the patient's tissue with respect to a particular therapy application.

5. The implantable medical device as recited in claim 4, wherein the particular therapy application comprises a therapy selected from the group consisting of a spinal cord stimulation (SCS) therapy, a neuromuscular stimulation therapy, a dorsal root ganglion (DRG) stimulation therapy, a deep brain stimulation (DBS) therapy, a cochlear stimulation therapy, a drug delivery therapy, a cardiac pacemaker therapy, a cardioverter-defibrillator therapy, a cardiac rhythm management (CRM) therapy, an electrophysiology (EP) mapping and radio frequency (RF) ablation therapy, an electroconvulsive therapy (ECT), a repetitive transcranial magnetic stimulation (rTMS) therapy, and a vagal nerve stimulation (VNS) therapy.

6. The implantable medical device as recited in claim 1, wherein the first AC coupling sense capacitor ($C_{SENSE1}$) terminal coupled to the first inactive electrode is coupled by the switching circuitry to the reference input of the ADC as the first Kelvin connection terminal.

7. The implantable medical device as recited in claim 6, wherein the second AC coupling sense capacitor ($C_{SENSE2}$) terminal coupled to the second active electrode is coupled by the switching circuitry to the sense input of the ADC as the second Kelvin connection terminal.

8. The implantable medical device as recited in claim 6, wherein the second DC blocking stimulation capacitor ($C_{DC2}$) terminal coupled to the second active electrode is coupled by the switching circuitry to the sense input of the ADC as the second Kelvin connection terminal.

9. The implantable medical device as recited in claim 1, wherein the second AC coupling sense capacitor ($C_{SENSE2}$) terminal coupled to the second active electrode is coupled by the switching circuitry to the sense input of the ADC as the second Kelvin connection terminal.

10. The implantable medical device as recited in claim 9, wherein the first DC blocking stimulation capacitor ($C_{DC1}$) terminal coupled to the first inactive electrode is coupled by the switching circuitry to the reference input of the ADC as the first Kelvin connection terminal.

11. A method of operating an implantable medical device having a pulse generator configured to supply stimulation to a patient's tissue for therapy, the method comprising:
    configuring a plurality of electrodes of an implantable lead system of the implantable medical device as at least one active electrode and at least one inactive electrode, wherein a first inactive electrode of the at least one inactive electrode is configured as not selected to stimulate with respect to the patient's tissue and is thereby inactive and a second active electrode of the at least one active electrode is configured as selected to stimulate with respect to the patient's tissue and is thereby active;
    switchably coupling a first direct current (DC) blocking stimulation capacitor ($C_{DC1}$) terminal coupled to the first inactive electrode or a first alternating current (AC) coupling sense capacitor ($C_{SENSE1}$) terminal coupled to the first inactive electrode as a first Kelvin connection terminal to a reference input of an analog-to-digital converter (ADC) forming diagnostic circuitry for a voltage measurement with respect to a second active electrode of the one or more active electrode;
    switchably coupling a second AC coupling sense capacitor ($C_{SENSE2}$) terminal coupled to the second active electrode or a second DC blocking stimulation capacitor ($C_{DC2}$) terminal coupled to the second active electrode as a second Kelvin connection terminal to a sense input of the ADC for the voltage measurement; and
    obtaining the voltage measurement across the first and second Kelvin connection terminals as a voltage indicative of a charge state accumulated across at least one of the $C_{DC2}$ capacitor coupled to the second active electrode or a double-layer (DL) capacitance ($C_{DL}$) associated with an electrode/tissue interface (ETI) of the second active electrode.

12. The method as recited in claim 11, further comprising setting a Kelvin connection selection mode to configure a plurality of switches to effectuate different combinations of voltage measurement connection paths between the terminals of the plurality of electrodes and the sense and reference inputs of the ADC of the diagnostic circuitry.

13. The method as recited in claim 12, further comprising configuring the first inactive electrode as a dedicated Kelvin electrode for facilitating at least one Kelvin connection path with respect to measuring voltages respectively associated with one or more active electrodes of the plurality of electrodes.

14. The method as recited in claim 12, further comprising configuring the second active electrode as one of a cathode to provide cathodic stimulation to the patient's tissue or an anode to provide anodic stimulation to the patient's tissue with respect to a particular therapy application.

15. The method as recited in claim 14, wherein the particular therapy application comprises a therapy selected from the group consisting of a spinal cord stimulation (SCS) therapy, a neuromuscular stimulation therapy, a dorsal root ganglion (DRG) stimulation therapy, a deep brain stimulation (DBS) therapy, a cochlear stimulation therapy, a drug delivery therapy, a cardiac pacemaker therapy, a cardioverter-defibrillator therapy, a cardiac rhythm management (CRM) therapy, an electrophysiology (EP) mapping and radio frequency (RF) ablation therapy, an electroconvulsive therapy (ECT), a repetitive transcranial magnetic stimulation (rTMS) therapy, and a vagal nerve stimulation (VNS) therapy.

16. The method as recited in claim 11, wherein the first AC coupling sense capacitor ($C_{SENSE1}$) terminal coupled to the first inactive electrode is coupled to the reference input of the ADC as the first Kelvin connection terminal.

17. The method as recited in claim 16, wherein the second AC coupling sense capacitor ($C_{SENSE2}$) terminal coupled to the second active electrode is coupled to the sense input of the ADC as the second Kelvin connection terminal.

18. The method as recited in claim 16, wherein the second DC blocking stimulation capacitor ($C_{DC2}$) terminal coupled to the second active electrode is coupled to the sense input of the ADC as the second Kelvin connection terminal.

19. The method as recited in claim 11, wherein the second AC coupling sense capacitor ($C_{SENSE2}$) terminal coupled to the second active electrode is coupled to the sense input of the ADC as the second Kelvin connection terminal.

20. The method as recited in claim 19, wherein the first DC blocking stimulation capacitor ($C_{DC1}$) terminal coupled to the first inactive electrode is coupled to the reference input of the ADC as the first Kelvin connection terminal.

* * * * *